United States Patent
Scirica et al.

(10) Patent No.: US 7,886,952 B2
(45) Date of Patent: *Feb. 15, 2011

(54) SURGICAL STAPLING APPARATUS WITH LOCKING MECHANISM

(75) Inventors: Paul A. Scirica, Huntington, CT (US); Stanislaw Marczyk, Stratford, CT (US)

(73) Assignee: Tyco Healthcare Group LP, North Haven, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/704,049

(22) Filed: Feb. 7, 2007

(65) Prior Publication Data

US 2007/0175948 A1 Aug. 2, 2007

Related U.S. Application Data

(63) Continuation-in-part of application No. 11/410,861, filed on Apr. 24, 2006, now abandoned, which is a continuation of application No. 11/059,975, filed on Feb. 17, 2005, now Pat. No. 7,097,089, application No. 11/704,049, which is a continuation-in-part of application No. 11/059,773, filed on Feb. 17, 2005, now Pat. No. 7,225,963.

(60) Provisional application No. 60/545,621, filed on Feb. 17, 2004, provisional application No. 60/545,622, filed on Feb. 17, 2004.

(51) Int. Cl.
*A61B 17/068* (2006.01)

(52) U.S. Cl. ............... 227/175.2; 227/175.1; 227/175.3

(58) Field of Classification Search ... 227/175.1–175.3, 227/19

See application file for complete search history.

(56) References Cited

U.S. PATENT DOCUMENTS

| 3,079,606 | A |   | 3/1963  | Bobrov et al. |          |
|-----------|---|---|---------|---------------|----------|
| 3,490,675 | A |   | 1/1970  | Green et al.  |          |
| 3,499,591 | A |   | 3/1970  | Green         |          |
| 4,244,372 | A |   | 1/1981  | Kapitanov et al. |       |
| 4,304,236 | A | * | 12/1981 | Conta et al.  | 227/179.1 |
| 4,429,695 | A |   | 2/1984  | Green         |          |
| 4,520,817 | A |   | 6/1985  | Green         |          |
| 4,589,413 | A |   | 5/1986  | Malyshev et al. |        |
| 4,605,001 | A |   | 8/1986  | Rothfuss et al. |        |

(Continued)

FOREIGN PATENT DOCUMENTS

DE 4300307 A1 7/1994

(Continued)

*Primary Examiner*—Rinaldi I. Rada
*Assistant Examiner*—Gloria R Weeks

(57) ABSTRACT

The present disclosure provides for a surgical stapling apparatus and/or a loading unit for use with and/or supportable on a distal end of a surgical stapling apparatus. The loading unit includes a housing portion including a distal end and a proximal end, a drive assembly slidably supported within the housing portion of the loading unit, and a locking mechanism supported on the housing portion of the loading unit. The locking mechanism has a first position wherein the locking mechanism engages the drive assembly and maintains the position of the drive assembly in a ready-to-load position relative to the housing portion of the loading unit. The locking mechanism is pivotable to a second position wherein the locking mechanism disengages the drive assembly and enables the drive assembly to move relative to the housing portion.

42 Claims, 33 Drawing Sheets

U.S. PATENT DOCUMENTS

| | | | |
|---|---|---|---|
| 4,608,981 A | 9/1986 | Rothfuss et al. |
| 4,610,383 A | 9/1986 | Rothfuss et al. |
| 4,633,861 A | 1/1987 | Chow et al. |
| 4,633,874 A | 1/1987 | Chow et al. |
| 4,672,964 A | 6/1987 | Dee et al. |
| 4,763,669 A | 8/1988 | Jaeger |
| 4,863,088 A | 9/1989 | Redmond et al. |
| 4,880,015 A | 11/1989 | Nierman |
| 4,892,244 A | 1/1990 | Fox et al. |
| 4,978,049 A | 12/1990 | Green |
| 4,991,764 A | 2/1991 | Mericle |
| 5,040,715 A | 8/1991 | Green et al. |
| 5,065,929 A | 11/1991 | Schulze et al. |
| 5,071,052 A | 12/1991 | Rodak et al. |
| 5,074,454 A | 12/1991 | Peters |
| 5,083,695 A | 1/1992 | Foslien et al. |
| 5,111,987 A | 5/1992 | Moeinzadeh et al. |
| 5,129,570 A | 7/1992 | Schulze et al. |
| 5,141,144 A | 8/1992 | Foslien et al. |
| 5,152,279 A | 10/1992 | Wilk |
| 5,209,747 A | 5/1993 | Knoepfler |
| 5,246,156 A | 9/1993 | Rothfuss et al. |
| RE34,519 E | 1/1994 | Fox et al. |
| 5,275,608 A | 1/1994 | Forman et al. |
| 5,282,826 A | 2/1994 | Quadri |
| 5,307,976 A | 5/1994 | Olson et al. |
| 5,312,023 A | 5/1994 | Green et al. |
| 5,318,221 A | 6/1994 | Green et al. |
| 5,326,013 A | 7/1994 | Green et al. |
| 5,330,502 A | 7/1994 | Hassler et al. |
| 5,332,142 A | 7/1994 | Robinson et al. |
| 5,350,391 A | 9/1994 | Iacovelli |
| 5,354,311 A | 10/1994 | Kambin et al. |
| 5,374,277 A | 12/1994 | Hassler |
| 5,376,095 A | 12/1994 | Ortiz |
| 5,383,888 A | 1/1995 | Zvenyatsky et al. |
| 5,397,046 A | 3/1995 | Savage et al. |
| 5,415,334 A | 5/1995 | Williamson, IV et al. |
| 5,415,335 A | 5/1995 | Knodell, Jr. |
| 5,433,721 A | 7/1995 | Hooven et al. |
| 5,465,895 A | 11/1995 | Knodel et al. |
| 5,467,911 A | 11/1995 | Tsuruta et al. |
| 5,474,566 A | 12/1995 | Alesi et al. |
| 5,474,571 A | 12/1995 | Lang |
| 5,484,451 A | 1/1996 | Akopov et al. |
| 5,486,185 A | 1/1996 | Freitas et al. |
| 5,487,500 A | 1/1996 | Knodel et al. |
| 5,507,426 A | 4/1996 | Young et al. |
| 5,527,318 A | 6/1996 | McGarry |
| 5,535,935 A | 7/1996 | Vidal et al. |
| 5,582,617 A | 12/1996 | Klieman et al. |
| 5,584,425 A | 12/1996 | Savage et al. |
| 5,605,272 A | 2/1997 | Witt et al. |
| 5,630,539 A | 5/1997 | Plyley et al. |
| 5,634,584 A | 6/1997 | Okorocha et al. |
| 5,762,255 A | 6/1998 | Chrisman et al. |
| 5,797,537 A | 8/1998 | Oberlin et al. |
| 5,799,857 A * | 9/1998 | Robertson et al. ......... 227/179.1 |
| 5,820,009 A | 10/1998 | Melling et al. |
| 5,878,938 A | 3/1999 | Bittner et al. |
| 5,893,506 A | 4/1999 | Powell |
| 5,901,895 A | 5/1999 | Heaton et al. |
| 5,993,506 A | 11/1999 | Kobayashi et al. |
| 6,010,054 A | 1/2000 | Johnson et al. |
| 6,032,849 A | 3/2000 | Mastri et al. |
| 6,109,500 A | 8/2000 | Alli et al. |
| 6,241,139 B1 | 6/2001 | Milliman et al. |
| 6,439,446 B1 | 8/2002 | Perry et al. |
| 6,953,139 B2 | 10/2005 | Milliman et al. |
| 7,044,352 B2 | 5/2006 | Shelton, IV et al. |
| 7,044,353 B2 | 5/2006 | Mastri et al. |
| 7,097,089 B2 | 8/2006 | Marczyk |
| 7,225,963 B2 * | 6/2007 | Scirica ................. 227/175.2 |
| 2004/0232201 A1 | 11/2004 | Wenchell et al. |
| 2005/0184123 A1 | 8/2005 | Scirica |
| 2005/0184124 A1 | 8/2005 | Scirica et al. |
| 2005/0184125 A1 | 8/2005 | Marczyk |

FOREIGN PATENT DOCUMENTS

| | | |
|---|---|---|
| EP | 0484677 A1 | 5/1992 |
| EP | 0589306 A2 | 3/1994 |
| EP | 0591946 A1 | 4/1994 |
| EP | 0592243 A2 | 4/1994 |
| EP | 0621009 A1 | 10/1994 |
| EP | 0656188 A2 | 6/1995 |
| EP | 1563794 A1 | 8/2005 |
| FR | 2681775 A1 | 4/1993 |

* cited by examiner

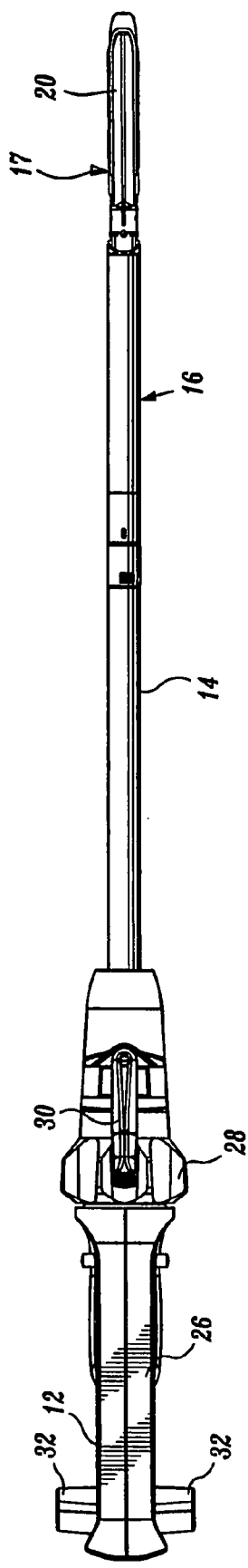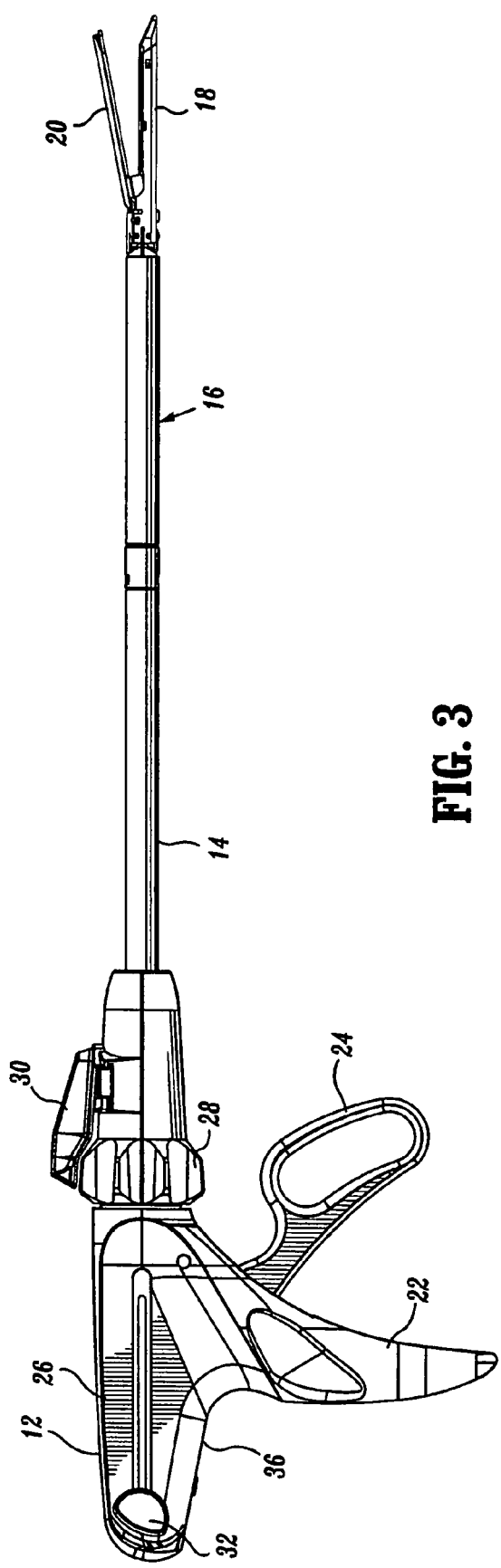
FIG. 2
FIG. 3

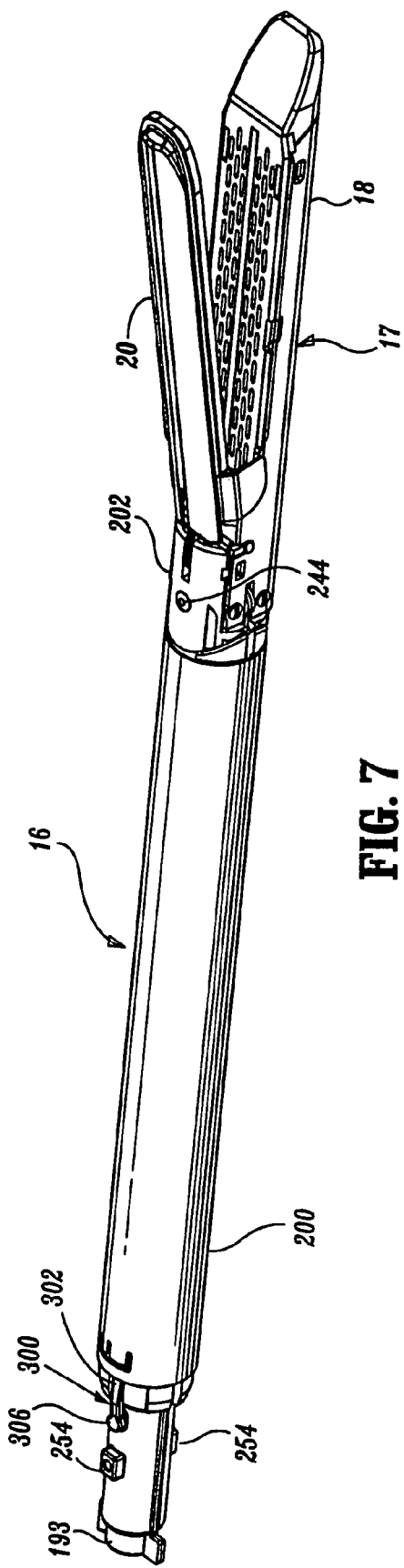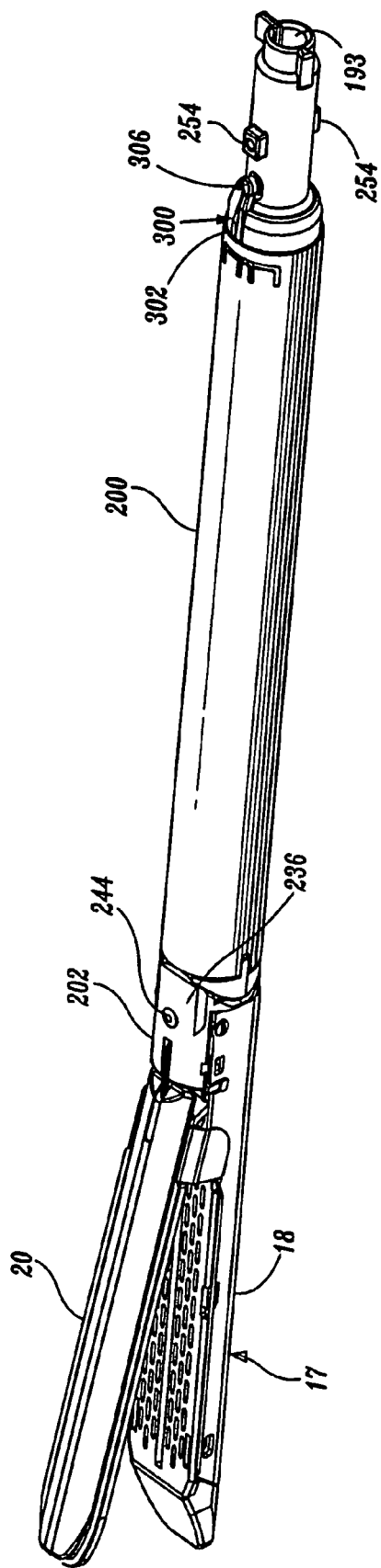
FIG. 7
FIG. 8

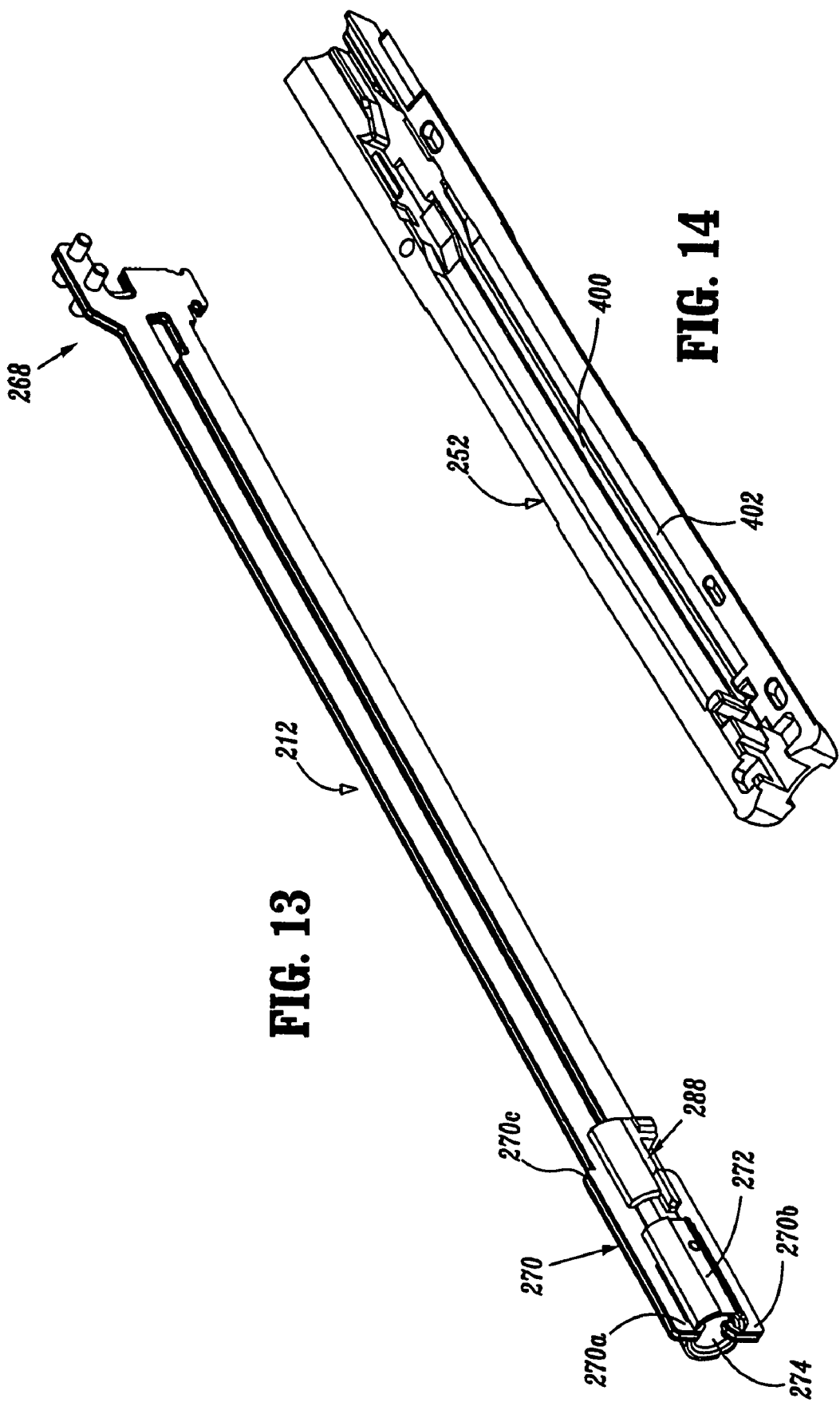

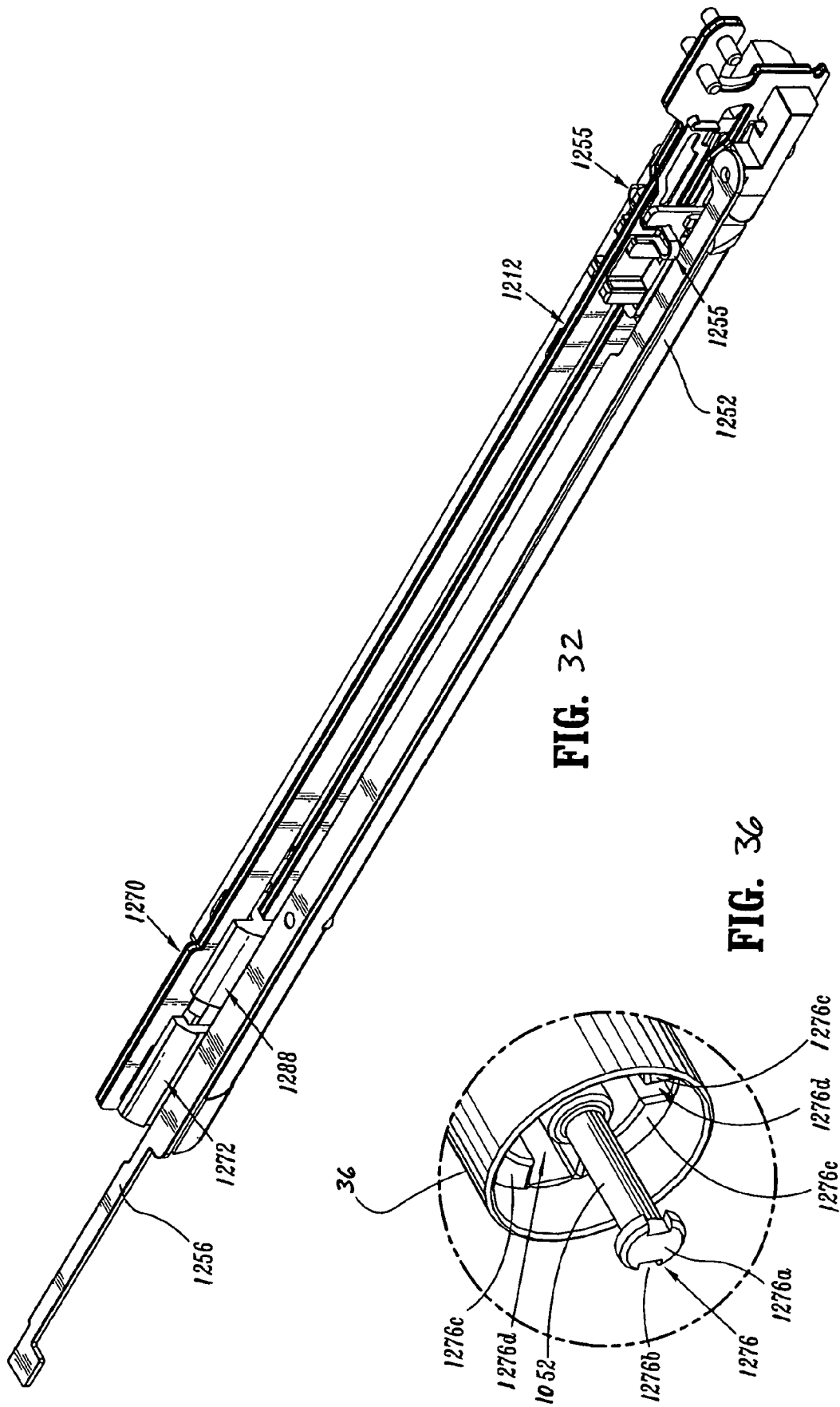

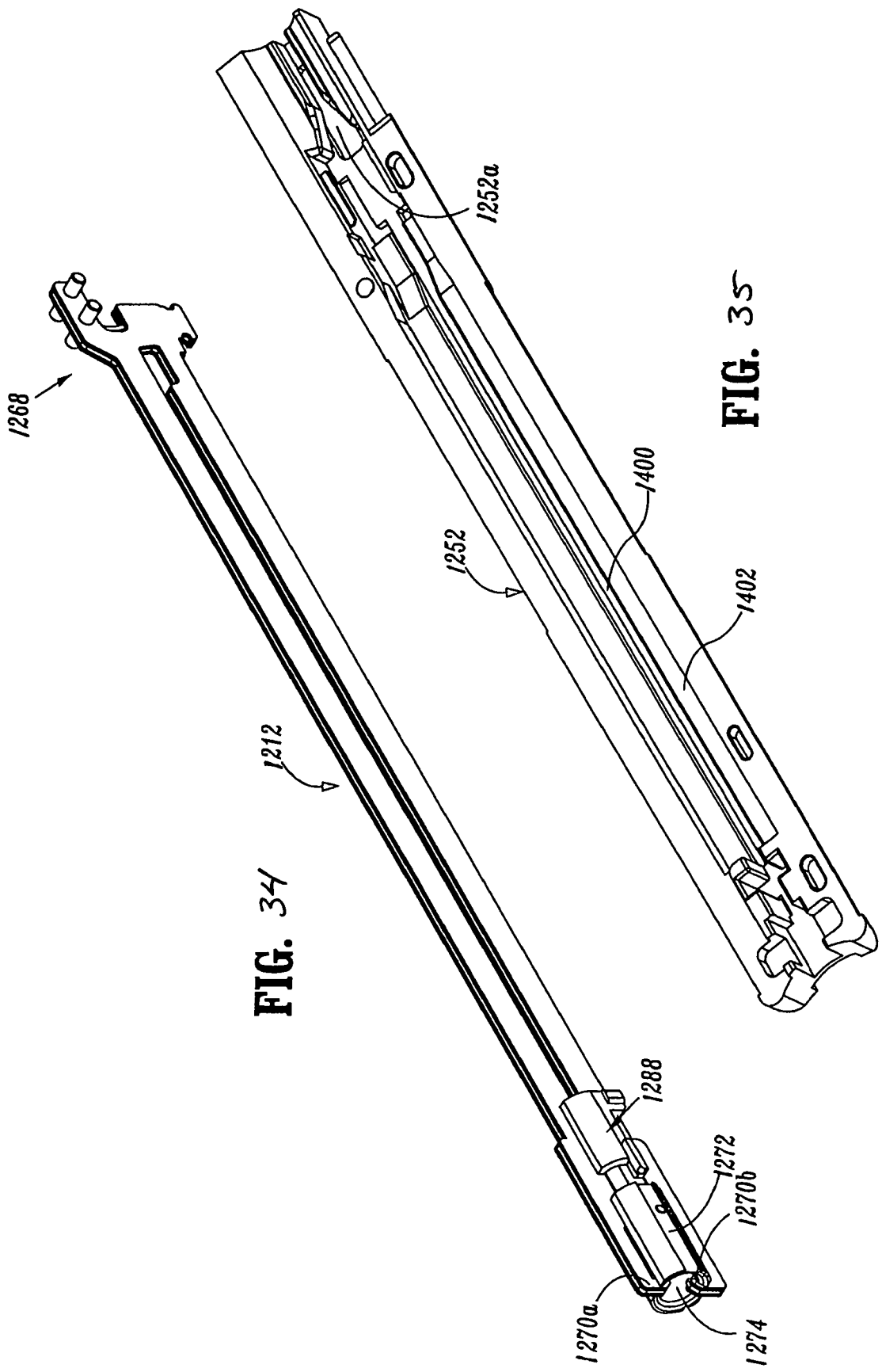

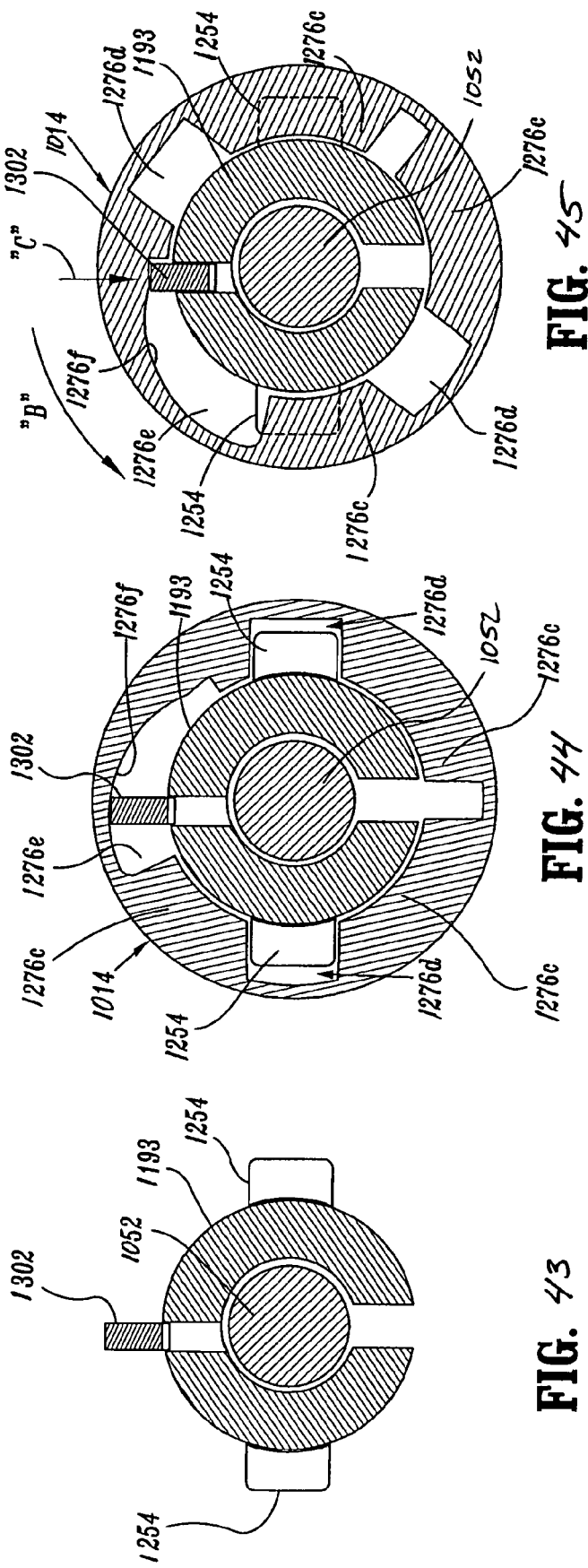

SURGICAL STAPLING APPARATUS WITH LOCKING MECHANISM

CROSS-REFERENCE TO RELATED APPLICATIONS

The present application is a Continuation-in-Part application which claims the benefit of and priority to U.S. application Ser. No. 11/410,861, filed Apr. 24, 2006, now abandoned which is a Continuation of U.S. application Ser. No. 11/059,975, filed Feb. 17, 2005, now U.S. Pat. No. 7,097,089, which claimed the benefit of and priority to U.S. Provisional Application Ser. No. 60/545,621, filed Feb. 17, 2004, the entire content of each of which being incorporated herein by reference.

The present Continuation-in-Part application is also a continuation application which claims the benefit of and priority to U.S. application Ser. No. 11/059,773, filed Feb. 17, 2005, now U.S. Pat. No. 7,225,963, which claimed the benefit of and priority to U.S. Provisional Application Ser. No. 60/545,622, filed Feb. 17, 2004, the entire content of each of which being incorporated herein by reference.

BACKGROUND

1. Technical Field

The present disclosure relates to a surgical apparatus, e.g., a surgical stapling apparatus. More particularly, the present disclosure relates to an endoscopic surgical stapling apparatus that includes a locking mechanism for retaining the drive assembly of a loading unit, e.g., a single use loading unit ("SULU") or disposable loading unit ("DLU"), at a substantially fixed axial position until the SULU or DLU has been loaded with or secured to a surgical stapling apparatus, to ensure proper or complete engagement of the SULU or DLU, especially its drive assembly, to the surgical stapling apparatus. For simplicity, hereinafter, SULU or DLU will be referred to as "DLU", but it should be understood to include either or both a DLU or SULU.

2. Background of Related Art

Surgical devices wherein tissue is first grasped or clamped between opposing jaw structure and then joined by surgical fasteners are well known in the art. In some instruments a knife is provided to cut the tissue which has been joined by the fasteners. The fasteners are typically in the form of surgical staples but two part polymeric fasteners can also be utilized.

Instruments for this purpose can include two elongated jaw members which are respectively used to capture or clamp tissue. Typically, one of the jaw members carries a staple cartridge which houses a plurality of staples arranged in at least two lateral rows while the other jaw member has an anvil that defines a surface for forming the staple legs as the staples are driven from the staple cartridge. Generally, the stapling operation is effected by cam members that travel longitudinally through the staple cartridge, with the cam members acting upon staple pushers to sequentially eject the staples from the staple cartridge. A knife can travel between the staple rows to longitudinally cut and/or open the stapled tissue between the rows of staples. Such instruments are disclosed, for example, in U.S. Pat. No. 3,079,606 and U.S. Pat. No. 3,490,675.

A later stapler disclosed in U.S. Pat. No. 3,499,591 also applies a double row of staples on each side of the incision. This patent discloses a surgical stapler that has a disposable loading unit in which a cam member moves through an elongate guide path between two sets of staggered staple carrying grooves. Staple drive members are located within the grooves and are positioned in such a manner so as to be contacted by the longitudinally moving cam member to effect ejection of the staples from the staple cartridge of the disposable loading unit. Other examples of such staplers are disclosed in U.S. Pat. Nos. 4,429,695 and 5,065,929.

Each of the instruments described above is designed for use in conventional surgical procedures wherein surgeons have direct manual access to the operative site. However, in endoscopic or laparoscopic procedures, surgery is performed through a small incision or through a narrow cannula inserted through small entrance wounds in the skin. In order to address the specific needs of endoscopic and/or laparoscopic surgical procedures, endoscopic surgical stapling devices have been developed and are disclosed in, for example, U.S. Pat. No. 5,040,715 (Green, et al.); U.S. Pat. No. 5,307,976 (Olson, et al.); U.S. Pat. No. 5,312,023 (Green, et al.); U.S. Pat. No. 5,318,221 (Green, et al.); U.S. Pat. No. 5,326,013 (Green, et al.); U.S. Pat. No. 5,332,142 (Robinson, et al.); and U.S. Pat. No. 6,241,139 (Milliman et al.), the entire contents of each of which are incorporated herein by reference.

Tyco Healthcare Group, LP, the assignee of the present application, has manufactured and marketed endoscopic stapling instruments, such as the Multifire ENDO GIA™ 30 and Multifire ENDO GIA™ 60 instruments, for a number of years. These instruments include a surgical stapling apparatus and a DLU. Typically, the DLU is attached to the apparatus immediately prior to surgery. After use, the DLU can be removed from the apparatus and a new DLU can be fastened to the apparatus to perform additional stapling and/or cutting operations. These instruments have provided significant clinical benefits. Nonetheless, improvements to these instruments are still possible.

It would be desirable to provide an improved DLU for a surgical stapling apparatus and an improved surgical stapling apparatus having the DLU loaded thereon.

It would also be desirable to provide a locking member for a DLU to assure proper loading of the DLU to the shaft of a surgical stapling apparatus.

Accordingly, it is an object of this disclosure to provide an improved DLU which locks or retains its drive assembly in proper position to be loaded onto the shaft of a surgical stapling apparatus (hereinafter referred to as the or a "ready-to-load position") until the DLU is loaded onto a surgical stapling apparatus to assure that when the DLU is loaded thereto, the drive assembly is properly engaged by, coupled to or connected to a drive member of the shaft, thereby helping to ensure proper operation of the DLU and the surgical stapling apparatus. For example, with the DLU loaded onto the surgical stapling apparatus, after firing of the surgical stapling apparatus, retraction of the control rod will unapproximate or open and/or unclamp the anvil and cartridge assemblies.

An object of the disclosure is to provide an improved DLU that includes a locking mechanism that retains the drive assembly in such a ready-to-load position until the DLU is loaded onto the surgical stapling apparatus.

Another object of the disclosure is to provide such a locking mechanism for a DLU.

Another object of the present disclosure is to provide a locking mechanism for a DLU and a DLU having a locking mechanism, such that firing of the surgical stapling apparatus is prevented unless and until the DLU is loaded onto the shaft of the surgical stapling apparatus.

Yet another object of the disclosure is to provide a DLU that, after firing, can be disconnected from the surgical stapling apparatus.

Yet another object of the disclosure is to provide a DLU that has only two conditions, one in which it is not loaded and its drive assembly is locked or retained in the ready-to-load position, and another in which the DLU is loaded onto the shaft of a surgical stapling apparatus and in which the drive assembly is unlocked and free to be actuated.

Still another object of the present disclosure is to provide the above objects in a roticulating, i.e., roticulable, DLU.

SUMMARY

In accordance with the present disclosure, a surgical apparatus, e.g., a surgical stapling apparatus and/or a loading unit for use with the surgical apparatus, including a locking mechanism for ensuring proper engagement of a disposable loading unit to an end of the surgical apparatus is provided. According to one aspect of the present disclosure the surgical apparatus comprises a housing including an elongate body extending therefrom; and a loading unit supportable on a distal end of the housing. The loading unit includes a housing portion including a distal end and a proximal end; a drive assembly slidably supported within the housing portion of the loading unit; and a locking mechanism pivotally supported on the housing portion of the loading unit. The locking mechanism has a first position wherein the locking mechanism engages a portion of the drive assembly and maintains the position of the drive assembly relative to the housing portion of the loading unit. The locking mechanism has a second position wherein the locking mechanism disengages the drive assembly and enables the drive assembly to move relative to the housing portion. The locking mechanism is configured for movement from the first position to the second position in response to a connection of the loading unit to the elongate body of the housing.

According to another aspect of the present disclosure the loading unit for use with and/or supportable on a distal end of an elongate body of a surgical stapling apparatus, comprises a housing portion including a distal end and an elongate body extending from the distal end thereof; a drive assembly slidably supported within the housing portion of the loading unit; and a locking mechanism pivotally supported on the housing portion of the loading unit. The locking mechanism has a first position wherein the locking mechanism engages a portion of the drive assembly and maintains the position of the drive assembly relative to the housing portion of the loading unit. The locking mechanism has a second position wherein the locking mechanism disengages the drive assembly and enables the drive assembly to move relative to the housing portion. The locking mechanism is configured for actuation from the first position to the second position in response to a connection of the loading unit to the elongate body of the surgical stapling apparatus.

In one embodiment, the locking mechanism may include a lever pivotally connected to the housing portion and defining a pivot point, the lever having a distal end extending distally of the pivot point and a proximal end extending proximally of the pivot point, the distal end of the lever including a hook formed therein for selectively engaging a portion of the drive assembly, wherein when the locking mechanism is in the first position the hook engages the portion of the drive assembly and when the locking mechanism is in the second position the hook is disengaged from the portion of the drive assembly.

When the locking mechanism is moved from the first position to the second position, the proximal end of the lever may be moved radially inward relative to a central longitudinal axis of the loading unit and the distal end of the lever is moved radially outward relative to the central longitudinal axis of the loading unit. The locking mechanism may be moved from the first position to the second position upon a coupling of the loading unit to a distal end of the elongate body.

The loading unit and the elongate body may be configured for twisting engagement with one another, wherein the locking mechanism is moved from the first position to the second position by a twisting action of the loading unit relative to the elongate body when the proximal end of the housing portion of the loading unit is inserted in to the distal end of the elongate body.

The locking mechanism may further include a biasing member operatively associated therewith. The biasing member may bias the lever to the first position.

When the locking mechanism is in the first position, the proximal end of the lever may extend radially beyond an outer surface of the housing portion. The proximal end of the lever of the locking mechanism may define an angled surface to facilitate connection with the elongate body.

The surgical apparatus may further include an elongate body extending from the housing. The elongate body may include a distal end configured and dimensioned to selectively receive the proximal end of the housing portion of the loading unit.

In another embodiment, the locking mechanism may include a lever having a distal end pivotally connected to the housing portion and a free proximal end; and a tooth extending radially inward from the lever, wherein the tooth selectively engages an engagement surface formed on the drive assembly such that when the locking mechanism is in the first position the tooth engages the engagement surface of the drive assembly and when the locking mechanism is in the second position the tooth is disengaged from the engagement surface of the drive assembly.

Accordingly, when the locking mechanism is moved from the first position to the second position, the lever may be pivoted about the distal end thereof such that a longitudinal axis of the lever is angled with respect to a longitudinal axis of the housing portion.

The locking mechanism may be moved from the first position to the second position by a projection extending radially inward of the elongate body. The projection may act on a side surface of the lever as the loading unit is twisted into loaded engagement in the elongate body.

When the locking mechanism is in the first position the lever may be substantially axially aligned with a nub extending radially outward from the proximal end of the housing portion and when the locking mechanism is in the second position the lever is out of axial alignment with the nub of the insertion tip.

The proximal end of the lever may include a nub extending toward the proximal end of the housing portion, and wherein the proximal end of the housing portion may include a recess formed in the surface thereof for receipt of the nub of the lever when the lever is in the first position.

The locking mechanism may further include a biasing member operatively associated therewith for maintaining the lever in the first position.

The surgical apparatus may be a stapler. The surgical apparatus may include an elongate body extending from the housing. The proximal end of the housing portion of the loading unit may define an insertion tip.

Additional advantages will become apparent from the description which follows, taken in conjunction with the accompanying drawings.

BRIEF DESCRIPTION OF THE DRAWINGS

The present disclosure will be further described with reference to the accompanying drawings, wherein like reference numerals refer to like parts in the several views, and wherein:

FIG. 2 is a top view of the surgical stapling apparatus shown in FIG. 1;

FIG. 3 is a side view of the surgical stapling apparatus shown in FIGS. 1 and 2;

FIG. 7 is a top perspective view of the DLU of FIG. 6;

FIG. 8 is a top perspective view of the DLU of FIGS. 6 and 7;

FIG. 13 is a top perspective view of the portion of the axial drive assembly of FIG. 11 of the DLU of FIGS. 6-9;

FIG. 14 is an enlarged top perspective view of a lower housing half of the housing portion of the DLU of FIGS. 6-9;

FIG. 32 is a top perspective view of the proximal housing portion and mounting assembly of the DLU of FIGS. 28-31 with the upper housing half removed;

FIG. 34 is a top perspective view of the axial drive assembly of FIG. 33 of the DLU of FIGS. 28-31;

FIG. 35 is an enlarged top perspective view of a lower housing half of the proximal housing portion of the DLU of FIGS. 28-31;

FIG. 36 is an enlarged perspective view of the distal end of the elongated body of the stapling apparatus shown in FIG. 26;

FIG. 43 is an enlarged transverse cross-sectional view of the proximal end of the DLU of FIGS. 28-31, as taken through 43-43 of FIG. 40;

FIG. 44 is an enlarged transverse cross-sectional view of the proximal end of the DLU of FIGS. 28-31, as taken through 44-44 of FIG. 42, illustrating the position of the locking mechanism prior to the rotation of the DLU relative to the elongate body; and FIG. 45 is an enlarged transverse cross-sectional view of the proximal end of the DLU of FIGS. 28-31, as would be taken through 44-44 of FIG. 42, illustrating the position of the locking mechanism following rotation of the DLU relative to the elongate body.

DETAILED DESCRIPTION OF PREFERRED EMBODIMENTS

Figure 1:
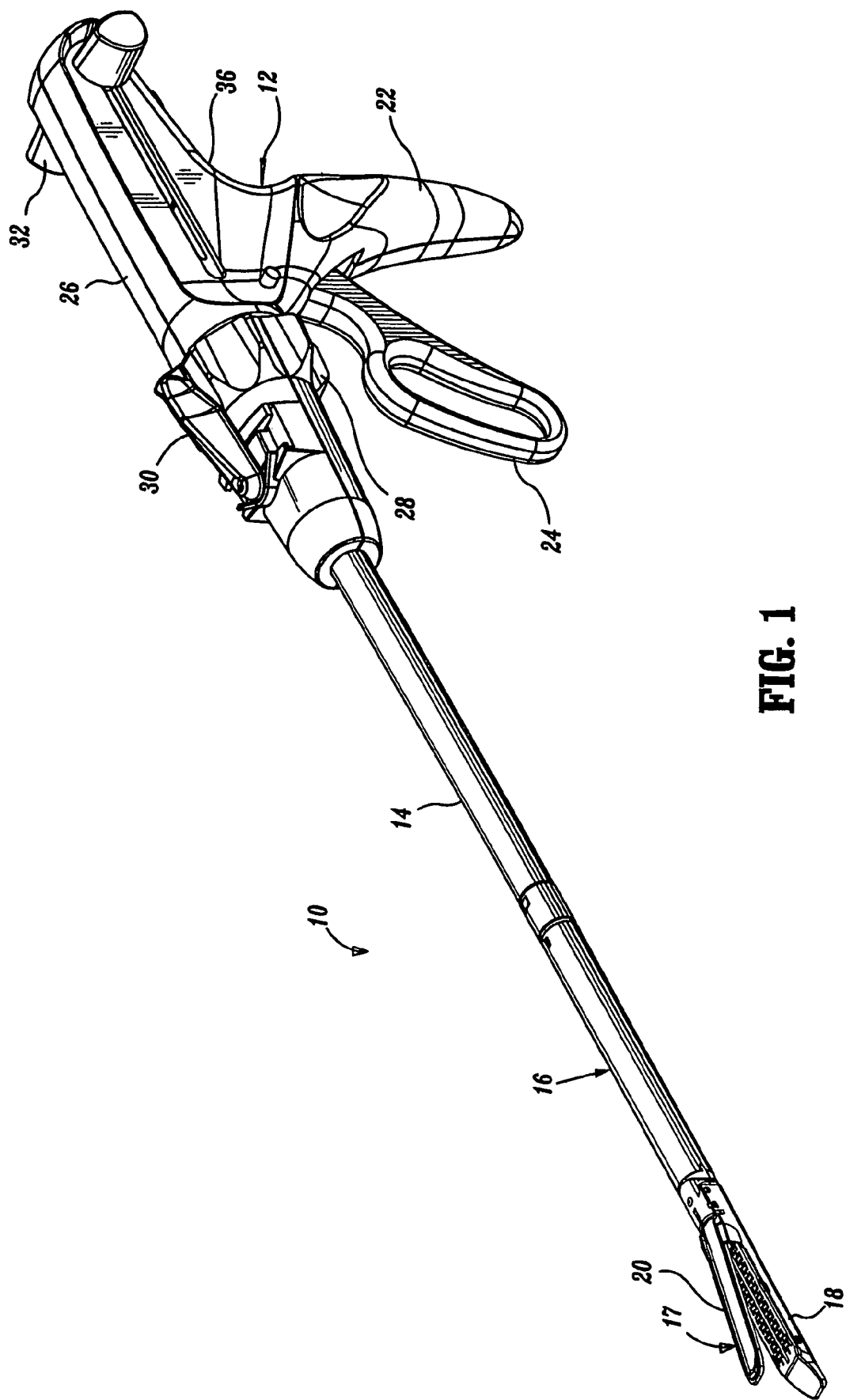
FIG. 1 is a top perspective view of a preferred embodiment of the presently disclosed surgical stapling apparatus.

Preferred embodiments of the presently disclosed surgical apparatus, DLU and locking mechanism or member will now be described in detail with reference to the drawings, in which like reference numerals designate identical or corresponding elements in each of the several views.

In the drawings and in the description that follows, the term "proximal", as is traditional, will refer to the end of the stapling apparatus which is closest to the operator, while the term "distal" will refer to the end of the apparatus which is furthest from the operator.

FIGS. 1-4 show a surgical apparatus, e.g., surgical stapling apparatus, generally referred to as 10. In the interest of brevity, this disclosure will focus primarily on systems, methods and structures for loading, engaging, coupling or connecting a disposable loading unit ("DLU") 16 to surgical stapling apparatus 10. A detailed discussion of the remaining components and method of use of surgical stapling apparatus 10, is disclosed in U.S. Pat. No. 6,241,139.

Surgical stapling apparatus 10 is an endoscopic apparatus and includes a handle assembly 12 and an elongated body 14 extending from handle assembly 12. A DLU 16 is releasably secured to the distal end of elongated body 14. While this disclosure relates to the use of a DLU with surgical stapling apparatus 10, it is understood and within the scope of the present disclosure that a single use loading unit (SULU) or other end effector and/or tool assembly can equally be used in cooperation with surgical stapling apparatus 10.

DLU 16 includes a tool assembly 17 having a cartridge assembly 18 housing a plurality of surgical staples (not shown) and an anvil assembly 20 movably secured in relation to cartridge assembly 18. As shown herein, DLU 16 is configured to apply six (6) linear rows of staples, each row in the DLU's measuring from about 30 mm to about 60 mm in length. DLUs for applying any number of rows of staples, having staple pockets arranged in various patterns and/or DLUs and end effectors having any other lengths, e.g., 45 mm, are also envisioned. Handle assembly 12 includes a stationary handle member 22, a movable handle member 24, and a barrel portion 26.

A rotatable member 28 preferably is mounted on the forward end of barrel portion 26 to facilitate rotation of elongated body 14 and attached DLU 16 with respect to handle assembly 12. An articulation lever 30 preferably is also mounted on the forward end of barrel portion 26 adjacent rotatable member 28 to facilitate articulation of tool assembly 17. Preferably, a pair of knobs 32 are movably positioned along barrel portion 26. Knobs 32 are advanced distally to approximate or close cartridge and/or anvil assembly 18, 20, and retracted proximally to unapproximate or open cartridge and/or anvil assembly 18, 20.

Figure 4:
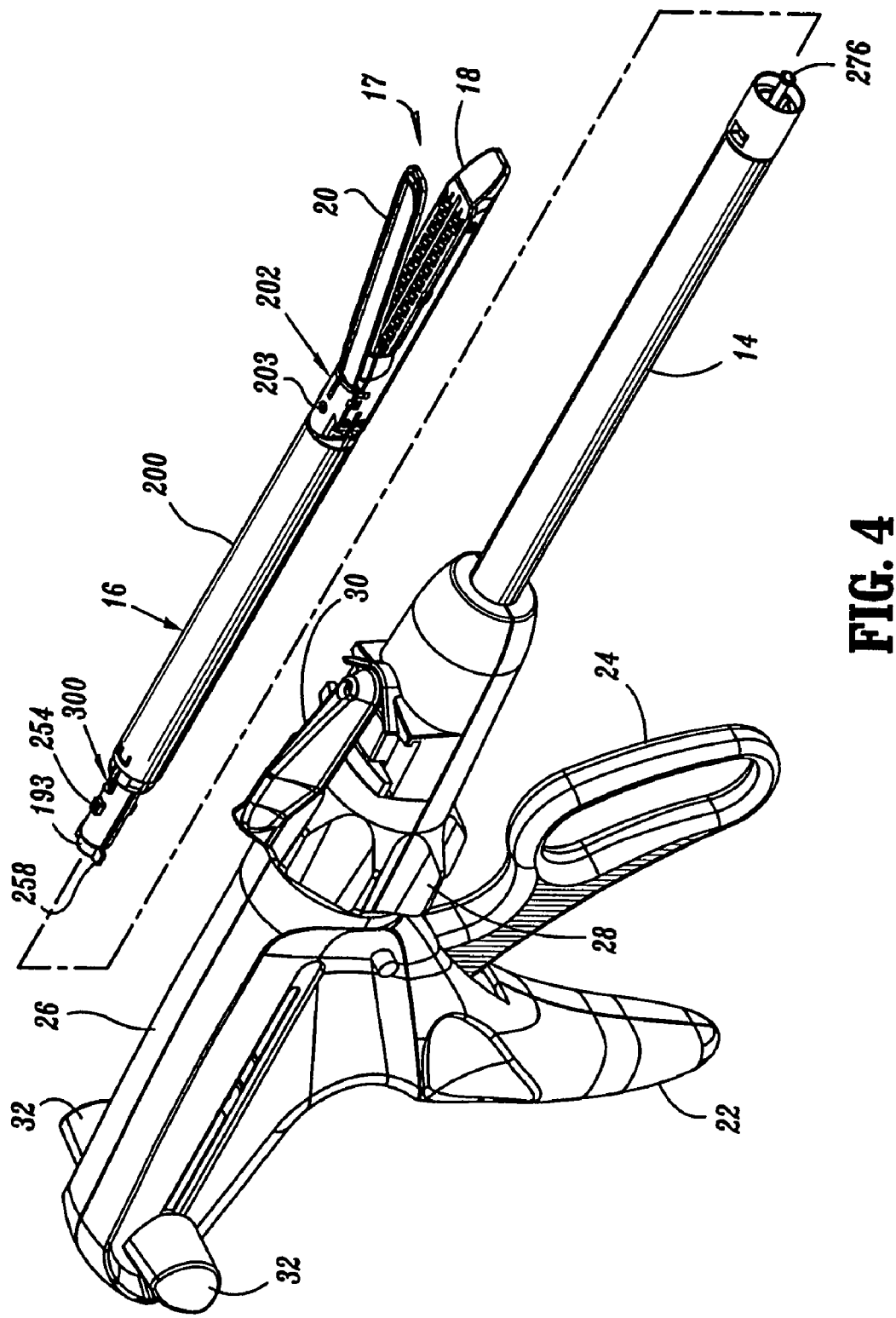
FIG. 4 is a top perspective view of the surgical stapling apparatus of FIGS. 1-3 with the DLU disengaged from the elongate body of the surgical stapling apparatus.

As seen in FIG. 4, DLU 16 is desirably selectively removably couplable to elongated body 14. DLU 16 includes a housing portion 200 having a proximal end adapted to releasably engage the distal end of elongated body 14. A mounting assembly 202 is pivotally secured at 203 to the distal end of housing portion 200, and is configured to receive the proximal end of tool assembly 17 such that pivotal movement of mounting assembly 202 about an axis at 203 perpendicular to the longitudinal axis of housing portion 200 effects articulation of tool assembly 17.

Figure 5:
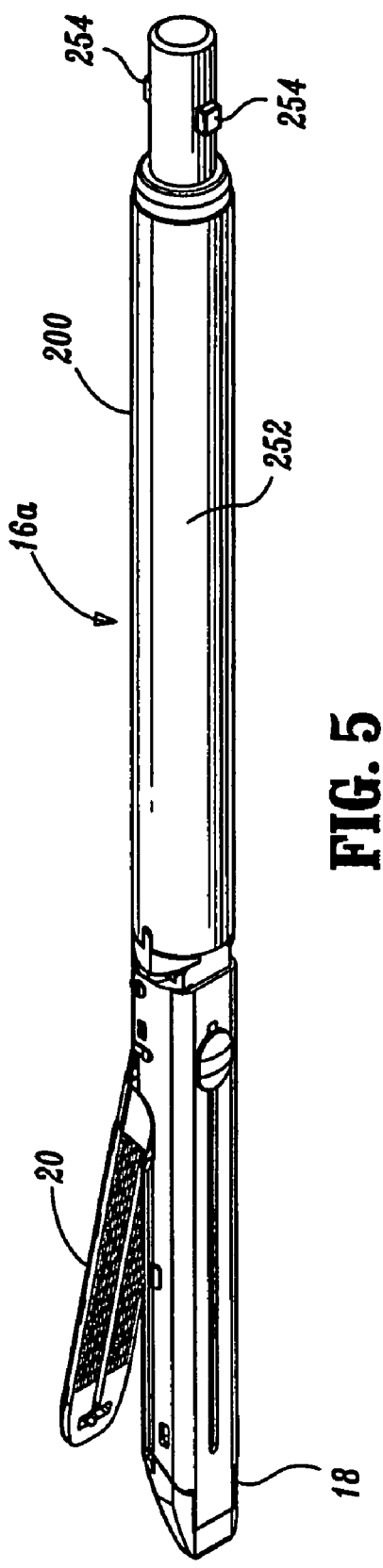
FIG. 5 is a bottom perspective view of a non-articulating DLU for use with the surgical stapling apparatus of FIGS. 1-4.
Figure 6:
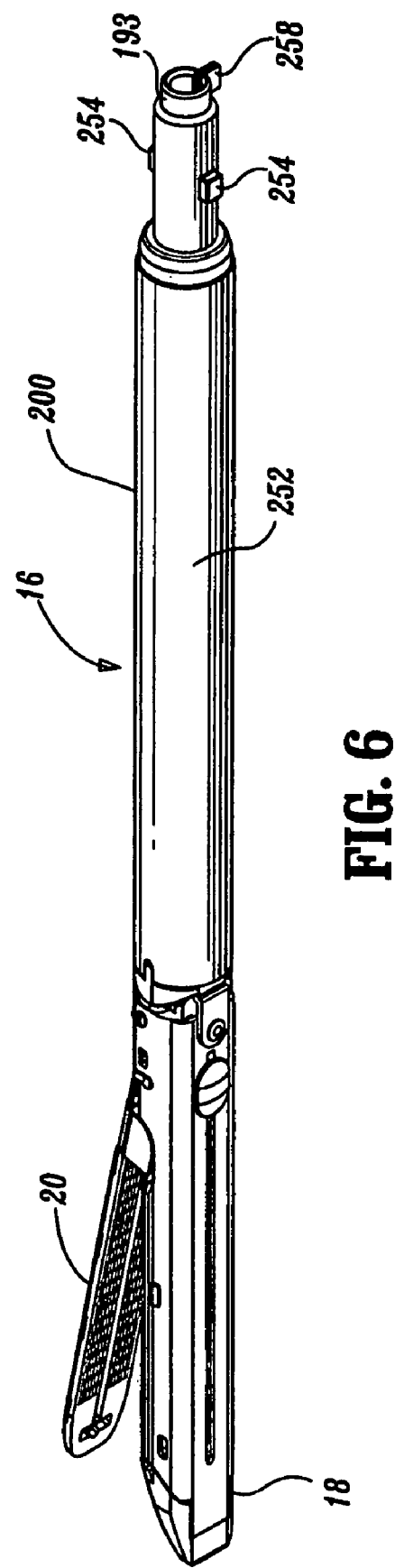
FIG. 6 is a bottom perspective view of the preferred articulating DLU of the surgical stapling apparatus of FIGS. 1-4.

FIGS. 5-8 show various perspective views of DLU 16. Surgical stapling apparatus 10 is capable of receiving a non-articulating DLU 16a, as seen in FIG. 5, or an articulating DLU 16, as seen in FIGS. 6-8. U.S. Pat. No. 6,241,139 includes a detailed discussion of articulating and non-articulating DLU.

With reference to FIGS. 9-14, DLU 16 includes a mounting assembly 235. Mounting assembly 235 includes an upper and a lower mounting portion 236, 238, respectively. A centrally located pivot member 284 extends from each of upper and lower mounting portions 236, 238 through respective openings 246a formed in coupling members 246. Coupling members 246 each include an interlocking proximal portion 246b configured to be received in grooves 290 formed in the distal end of upper and lower housing halves 250, 252 to retain mounting assembly 235 and upper and lower housing halves 250, 252 in a longitudinally fixed position in relation to each other.

Upper housing half 250 and lower housing half 252 are contained within an outer sleeve, shell or casing 251. The proximal end of upper housing half 250 includes an insertion tip 193 extending proximally therefrom. Insertion tip 193 includes engagement nubs 254, preferably a pair of diametrically opposed engagement nubs 254, extending radially outwardly therefrom, for releasably engaging the distal end of body 14. Nubs 254 form a bayonet-type coupling with the distal end of body 14. Housing halves 252 and 254 define a channel 400 for slidably receiving axial drive assembly 212 therein. An articulation link 256 is dimensioned to be slidably positioned within a slot 402 formed in upper and lower housing halves 250, 252. A pair of blow out plate assemblies 255 are positioned adjacent the distal end of housing portion 200 adjacent the distal end of axial drive assembly 212 to prevent outward buckling and bulging of drive assembly 212 during articulation and firing of surgical stapling apparatus 10. For a detailed discussion of the structure and operation of blow out plate assemblies 255, reference is made to International Application Serial No. PCT/US02/32031, filed on Oct. 4, 2002, entitled "Surgical Stapling Device", the entire content of which is herein incorporated by reference.

Figure 9:
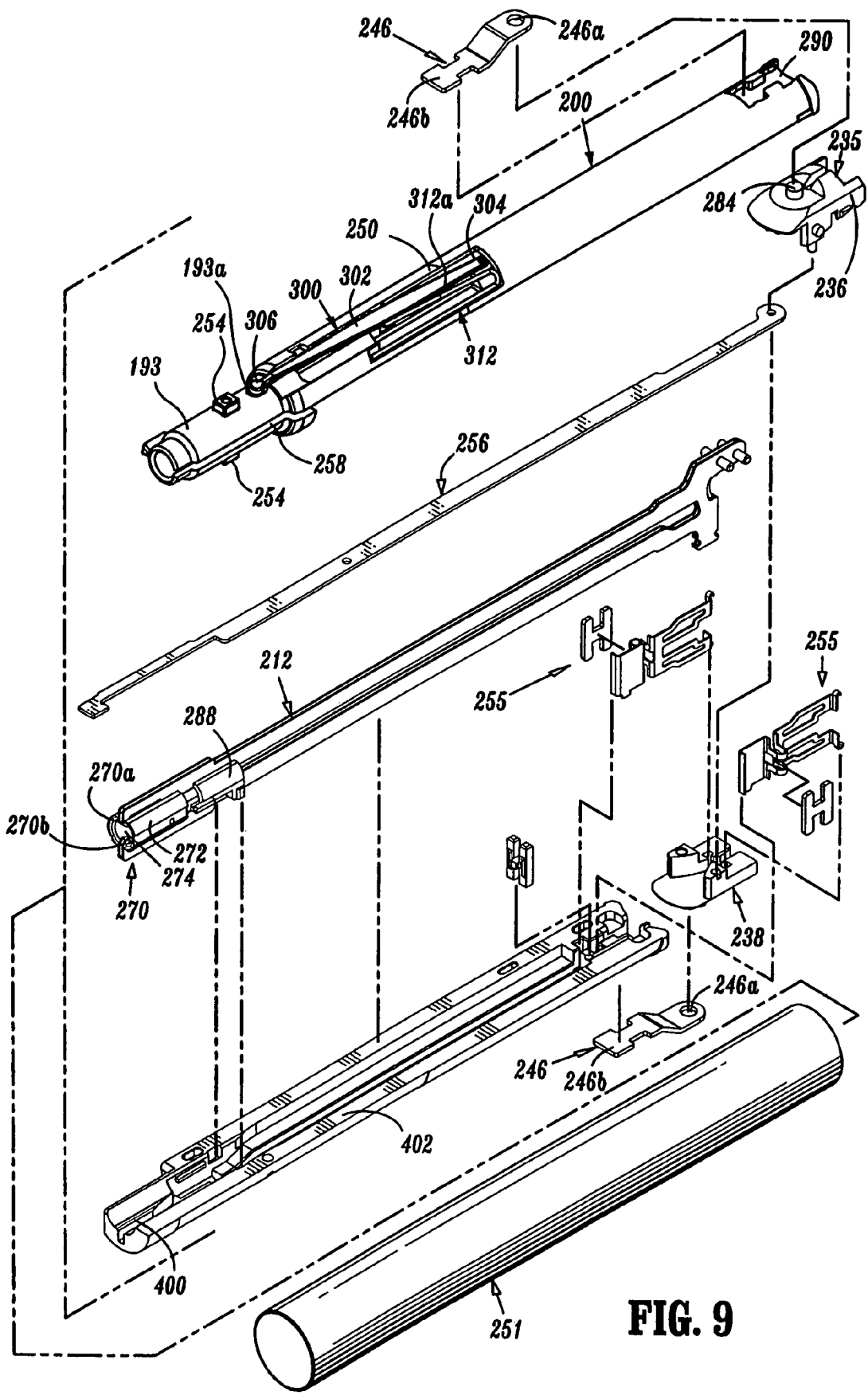
FIG. 9 is a top perspective view, with parts separated, of the proximal housing portion and mounting assembly of the DLU of FIGS. 6-8.
Figure 10:
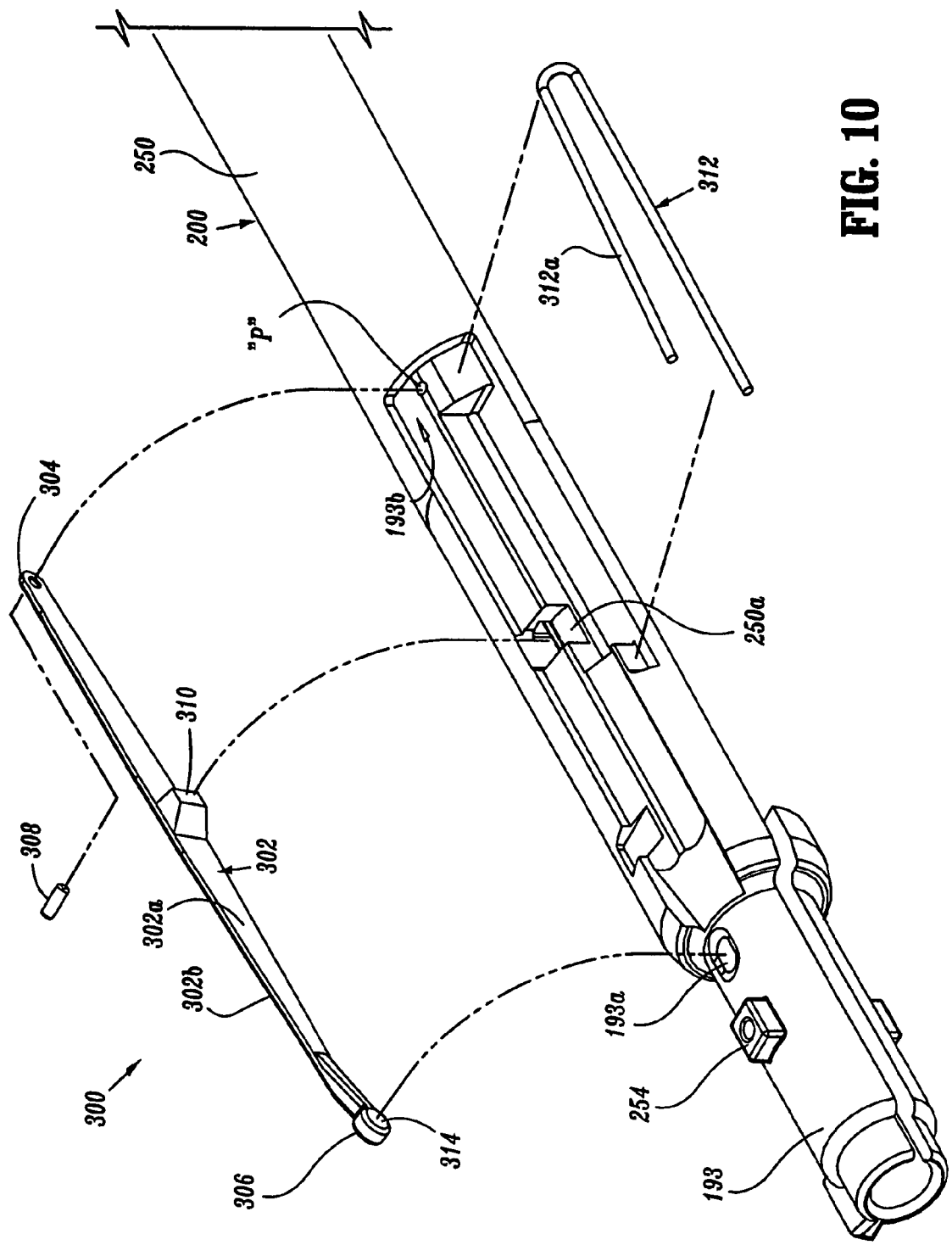
FIG. 10 is an enlarged top perspective view, with parts separated, of a proximal portion of the upper housing half of the DLU of FIGS. 6-9.

Referring to FIG. 9, optionally, a locking member 288 may be supported on engagement section 270 of axial drive assembly 212. In operation, when axial drive assembly 212 is actuated, by applying a predetermined force to movable handle member 24 to advance axial drive assembly 212 distally, locking member 288 provides an audible and tactile indication that surgical stapling apparatus 10 has been actuated. For a detailed discussion of the structure and operation of locking member 288, reference is made to the aforementioned International Application Serial No. PCT/US02/32031. Locking member 288 may also prevent inadvertent partial actuation of DLU 16, such as during shipping, by locking axial drive assembly 212 at a fixed position within DLU 16 until a predetermined axial force has been applied to axial drive assembly 212.

Figure 11:
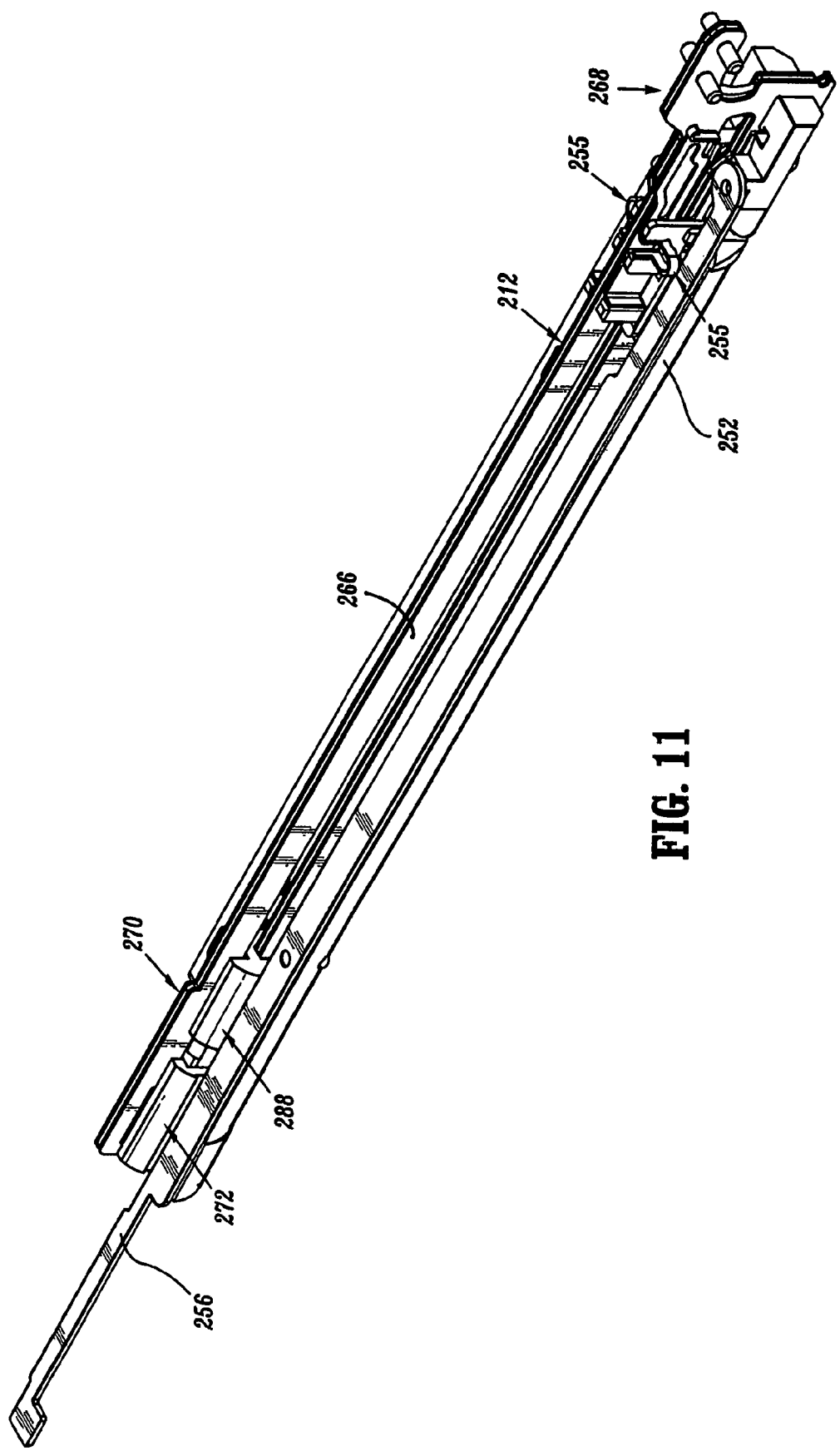
FIG. 11 is a top perspective view of the proximal housing portion and mounting assembly of the DLU of FIGS. 6-9 with the upper half of housing portion removed.
Figure 12:
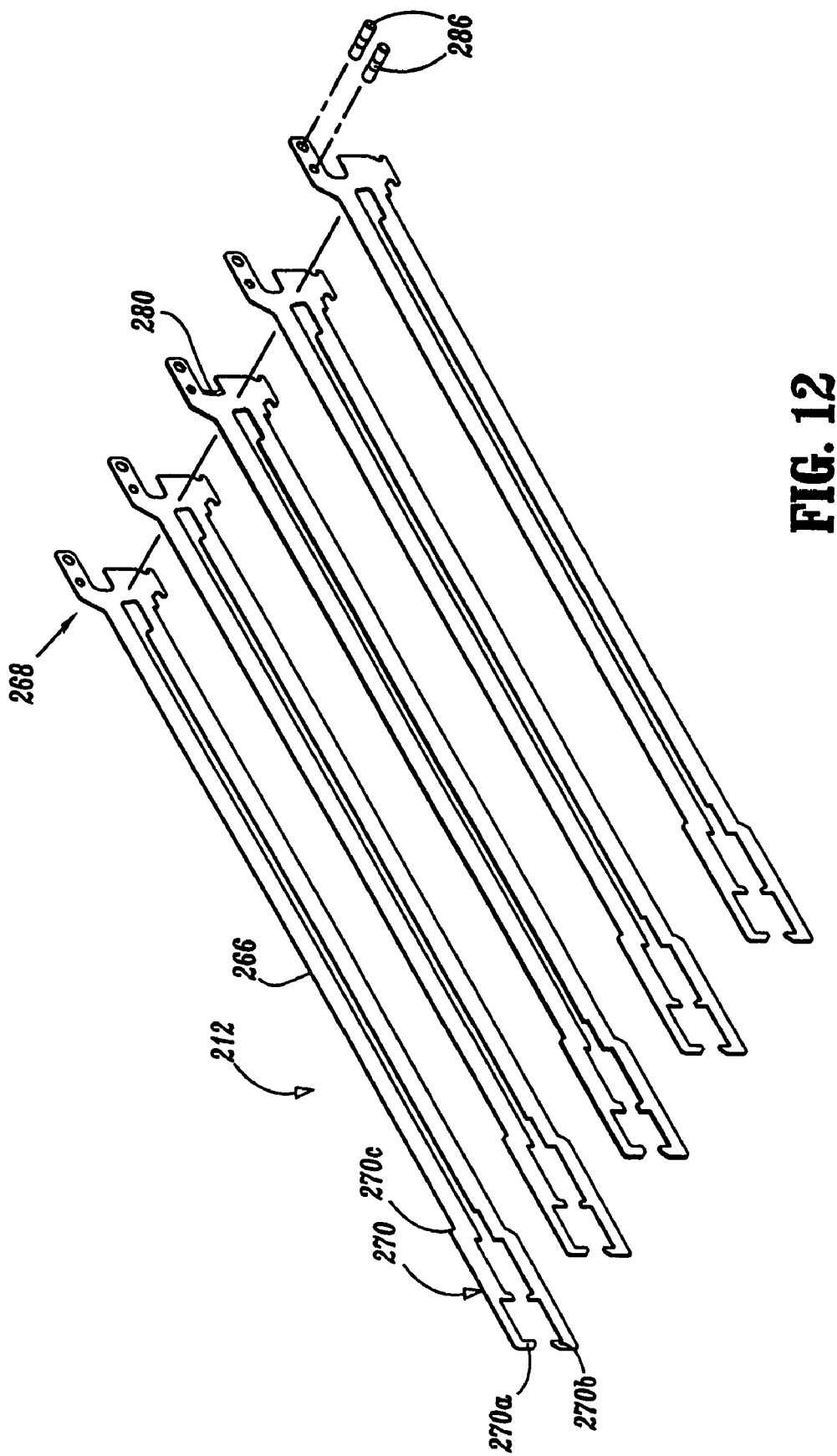
FIG. 12 is a top perspective view, with parts separated, of a portion of the axial drive assembly of the DLU of FIGS. 6-9.
Figures 15, 15A:
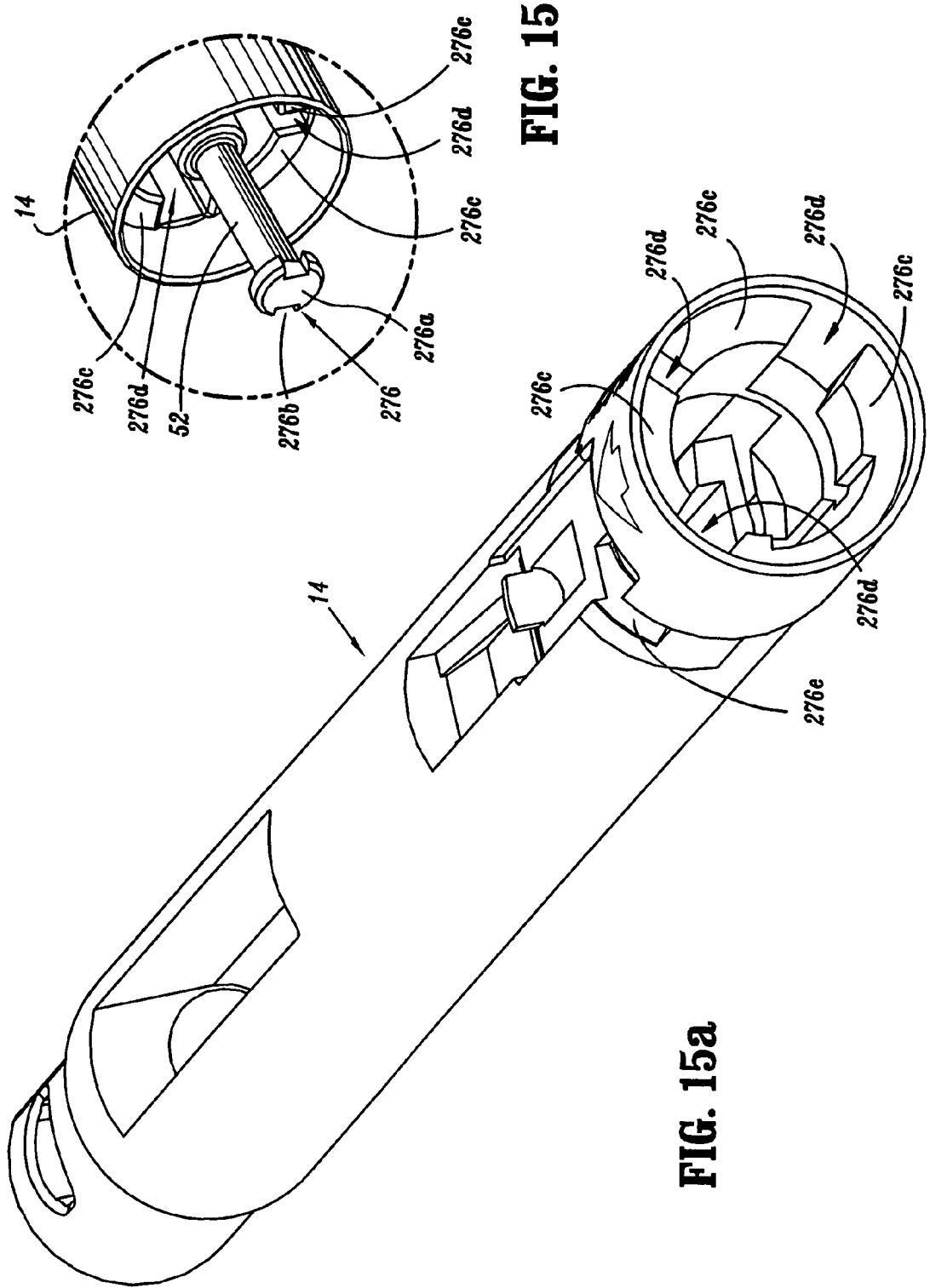
FIG. 15 is an enlarged perspective view of the distal end of the elongated body of the stapling apparatus shown in FIGS. 1-4, shown with the control rod extending therethrough.
FIG. 15a is an enlarged perspective view of the distal end of the elongate body of FIG. 15, shown without the control rod extending therethrough.

With reference to FIGS. 9-12, axial drive assembly 212 includes an elongated drive beam 266 (FIGS. 11 and 12) including a distal working head 268 (FIGS. 11 and 12) and a proximal engagement section 270. Drive beam 266 may be constructed from a single sheet of material or, preferably, multiple stacked sheets, as shown in FIG. 11. Engagement section 270 includes a pair of resilient engagement fingers 270a and 270b which are dimensioned and configured to mountingly engage a pair of corresponding retention slots 272a and 272b formed in drive member 272 (FIGS. 11 and 13). Drive member 272 includes a proximal porthole 274 configured to receive distal end 276 of a drive member, e.g., drive rod or control rod 52 (FIGS. 15 and 20-22) when the proximal end of DLU 16 is being engaged with elongated body 14 of surgical stapling apparatus 10. Control rod 52 functions to impart axial movement of drive assembly 212 from handle assembly 12.

As seen in FIGS. 9, 10 and 16-22, DLU 16 further includes a locking mechanism 300, preferably, pivotably supported on upper housing half 250. Locking mechanism 300 is manipulatable from a first position, in which drive assembly 212 is maintained in a ready-to-load position, to a second position, in which drive assembly 212 is free to move. DLU 16 is considered to be loaded to elongate body 14 when locking mechanism 300 is in the second position, i.e., when drive assembly 212 is connected to control rod 52 of elongate body 14. Locking mechanism 300 includes a lever 302 including a distal end 304 pivotally connected to upper housing half 250 and a free proximal end 306 in operative association with an outer surface of insertion tip 193. Desirably, distal end 304 is pivotably connected to upper housing half 250, via a pin 308 or preferably a ball-type pivot member. Alternatively, other known pivot structures formed integrally with or separate from upper housing half 250 may be used. Lever 302 further includes a projection, here shown as a tooth 310, extending radially inwardly from the inner surface of lever 302, preferably at a location between distal end 304 and proximal end 306.

In use, as best seen in FIGS. 16-22, when locking mechanism 300 is in the first position (i.e., in a ready-to-load, locked, or coupled position) (FIGS. 16, 17, 18, 20 and 21), lever 302 is substantially axially aligned with a longitudinal axis of housing portion 200 such that tooth 310 passes through an aperture 250a formed in upper housing half 250 and is engaged with an engagement surface, e.g., a notch, shoulder or recess 270c formed in the edge of engagement section 270 of drive assembly 212 to thereby effectively lock and maintain drive assembly 212 in the ready-to-load position wherein drive assembly 212 is in a retracted or proximal-most position relative to upper housing half 250. When DLU 16 is being coupled to the distal end of body 14, locking mechanism 300 ensures that engagement section 270 of drive assembly 212 is in a position to and properly engages, coupled with or connects to distal end 276 of control rod 52 (see FIGS. 20-22) of surgical stapling apparatus 10. Distal end 276 of control rod 52 has one or more engagement surfaces, preferably, and here shown as, including a head 276a and a smaller diameter annular recess 276b just proximal of head 276a and partially defined by head 276a. Thereafter, less preferably concomitantly therewith, locking mechanism 300 is manipulated (here rotated) to the second position wherein drive assembly 212 is in an unlocked, operative position in which lever 302 is angled with respect to the longitudinal axis of housing portion 200 such that tooth 310 is released from and/or otherwise disengaged from engagement surface 270c of engagement section 270 of drive assembly 212 to free drive assembly 212 to move relative to housing portion 212, here, upper and lower housing portion 250, 252 of DLU 16.

When locking mechanism 300 is in the second position, DLU is considered loaded onto ad/or into elongate body 14 of surgical stapling apparatus 10. Thus, drive assembly 212 is free to be actuated and reciprocated axially by drive rod 52 to perform its operative functions of approximating and closing anvil and cartridge assemblies 18, 20, driving knife 280 and firing staples, as well as of un-approximating, un-clamping, and retracting drive assembly 212. DLU 16 is considered to be loaded to elongate body 14 when locking mechanism 300 is in the second position, i.e., when drive assembly 212 is connected to control rod 52 of elongate body 14.

With continued reference to FIGS. 15-20, preferably lever 302 of locking mechanism 300 further includes a nub or detent 314 extending radially inward from an inner surface 302a of distal end 306 of lever 302. In use, nub 314 selectively engages and disengages a recess or dimple 193a formed in the outer surface of insertion tip 193. Preferably, dimple 193a is substantially in axial alignment with nubs 254 extending radially outward from insertion tip 193. Nub 314 and dimple 193a create a snap-fit type engagement wherein nub 314 and dimple 193a cooperate with one another to prevent and/or otherwise inhibit locking mechanism 300 from inadvertently or prematurely pivoting from the first position to the second position and thereby disengaging drive assembly 212. Locking mechanism 300 thus can include nub 314 and dimple 193a.

Figure 16:
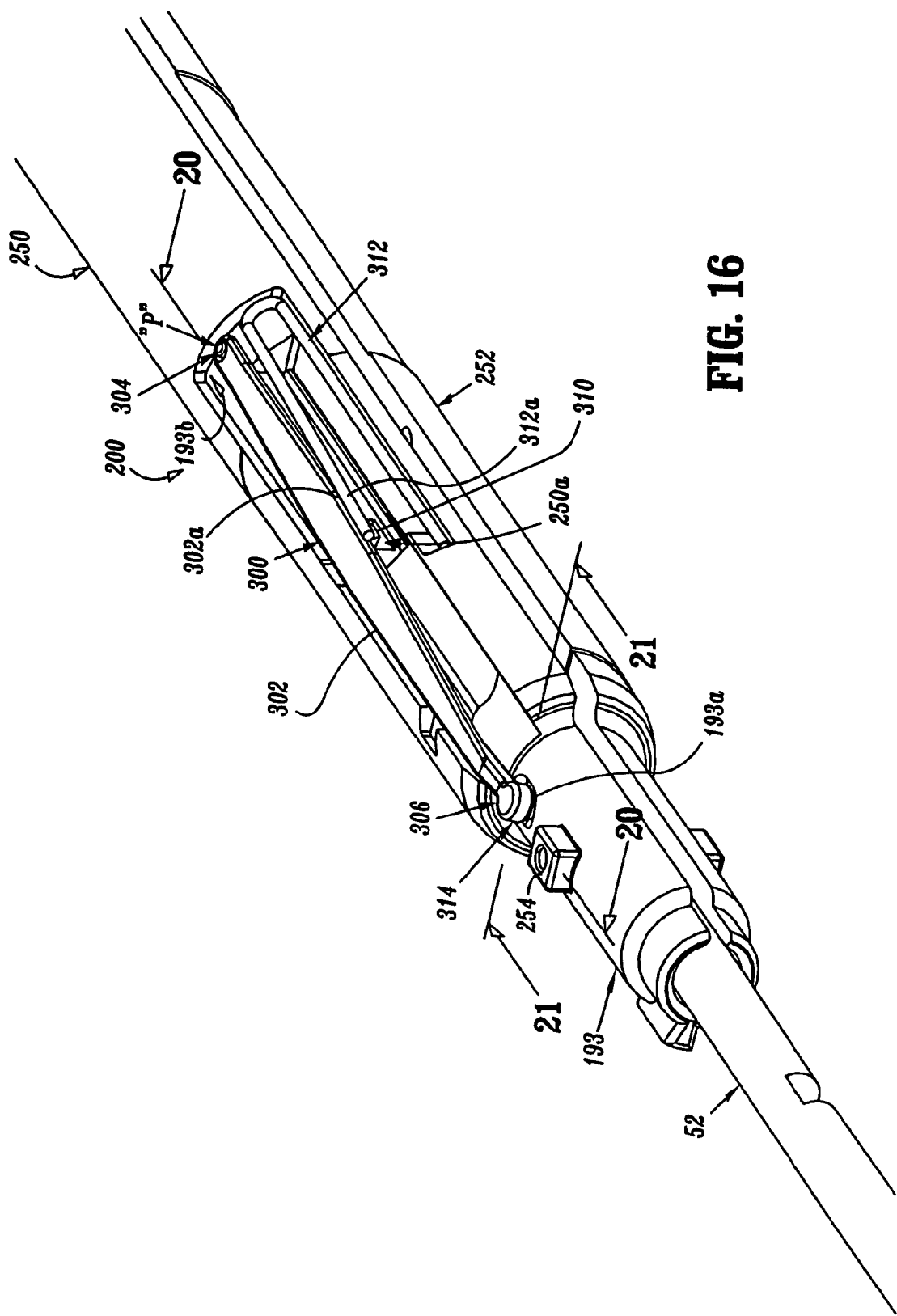
FIG. 16 is an enlarged perspective view of the proximal end of the DLU of FIGS. 6-9 illustrating a locking mechanism according to the present disclosure.
Figure 17:
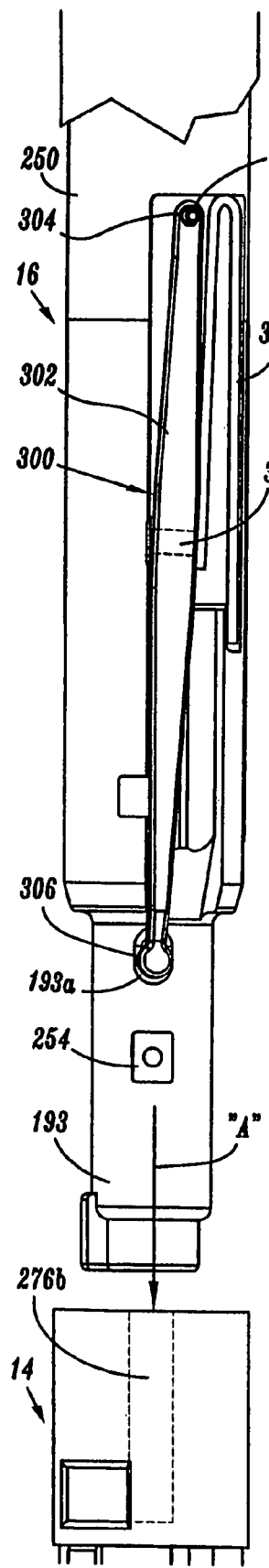
FIG. 17 is an enlarged top plan view with portions broken away illustrating a stage in the attachment of the DLU of FIGS. 6-9 to the elongate body of the surgical stapling apparatus shown in FIGS. 1-3.
Figure 18:
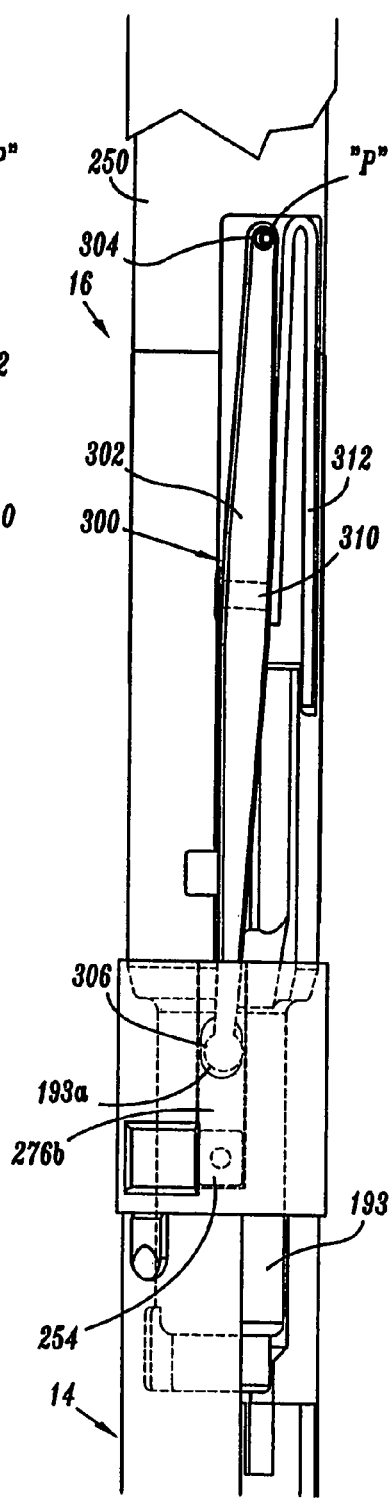
FIG. 18 is an enlarged top plan view with portions broken away illustrating another stage in the attachment of the DLU of FIGS. 6-9 to the elongate body of the surgical stapling apparatus shown in FIGS. 1-3.
Figure 19:
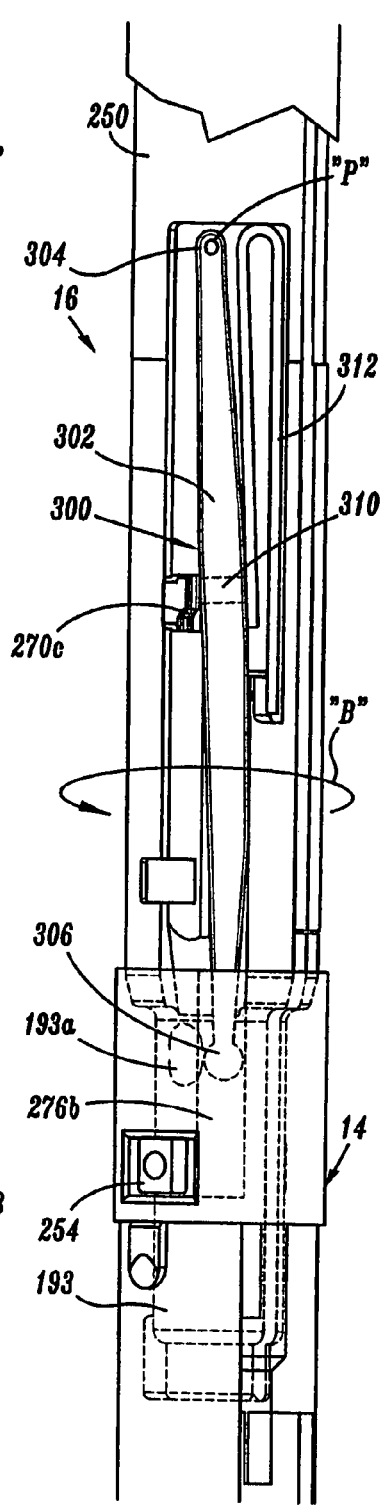
FIG. 19 is an enlarged top plan view with portions broken away illustrating yet another stage in the attachment of the DLU of FIGS. 6-9 to the elongate body of the surgical stapling apparatus shown in FIGS. 1-3.
Figure 20:
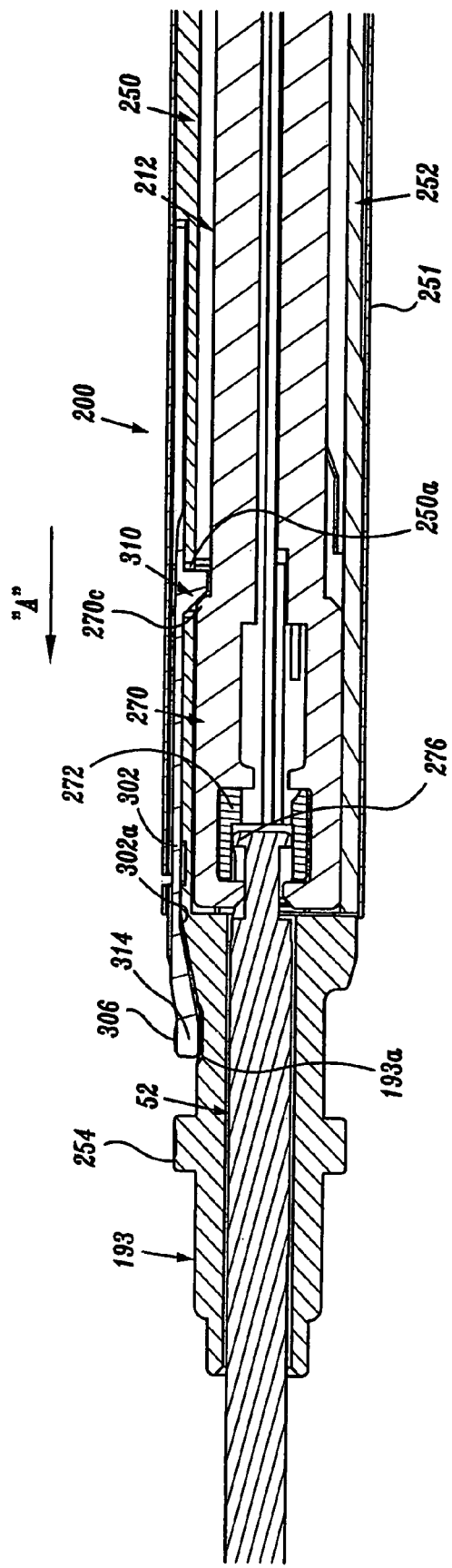
FIG. 20 is a longitudinal cross-sectional view of the proximal end of the DLU of FIGS. 6-9 as taken along line 20-20 of FIG. 16.

Preferably, insertion tip 193 includes a recessed area 193b (FIGS. 10 and 16) formed therein such that locking mechanism 300 does not extend radially outward beyond the outer surface of upper housing half 250. Lever 302 is able to pivot an amount sufficient to allow tooth 310 to disengage engagement surface or shoulder 270c of engagement section 270 of drive assembly 212 when locking mechanism 300 is in the second position. Locking mechanism 300 preferably includes a spring or other biasing means 312 in operative association with lever 302 and housing portion 200 mounted and/or positioned in such a manner so as to bias lever 302 to the first position. As seen in FIG. 16, spring 312 includes an arm 312a in contact with a side surface 302a of lever 302 thereby tending to maintain lever 302 in the first position. The twisting force applied with respect to DLU 16 and/or elongate body 14 of surgical stapling apparatus 10 is sufficient to overcome the bias of spring 312 to allow lever 302 to move to the second position.

With continued reference to FIGS. 15-20, a method of use and/or operation of locking mechanism 300, in securing DLU 16 to the distal end of elongate body 14, will be discussed. Initially, with locking mechanism 300 in the first position such that tooth 310 is in locking engagement with shoulder 270c of engagement section 270, to ensure that drive assembly 212 is in the proper position (e.g., in the proximal-most position) for coupling with head 276a of distal end 276 of control rod 52, insertion tip 193 of DLU 16 is introduced longitudinally into the distal end of elongate body 14, in the direction of arrow "A", such that nubs 254 slide into channels 276d, through and past projections 276c (see FIGS. 15 and 15a) extending radially inward from elongate body 14 of surgical stapling apparatus 10 near the distal end thereof.

Figure 21:
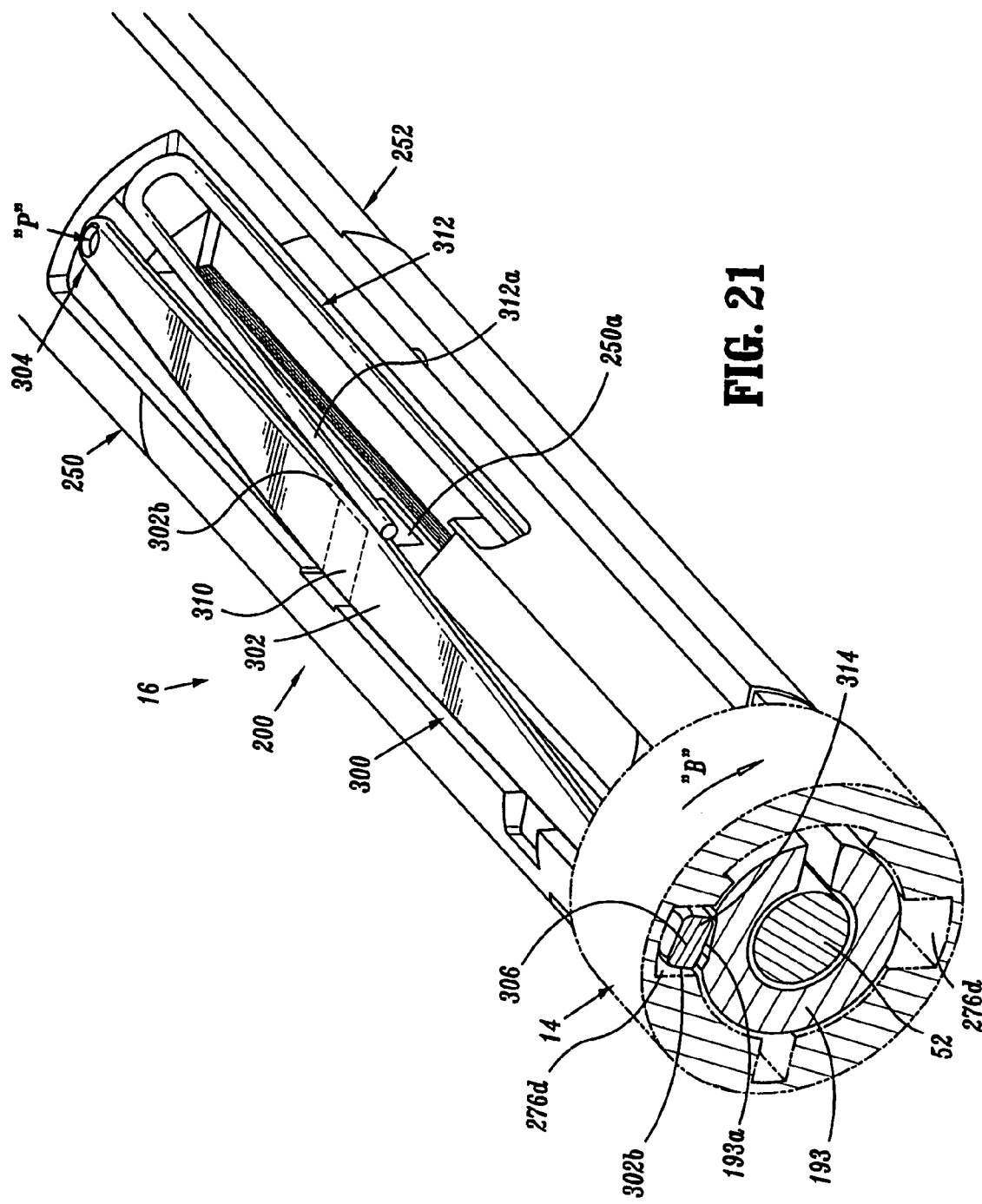
FIG. 21 is an enlarged transverse cross-sectional view of the proximal end of the DLU of FIGS. 6-9 with the distal end of the elongate body on the proximal end of the DLU as would be taken along 21-21 of FIG. 16, illustrating the locking mechanism in the first position.
Figure 22:
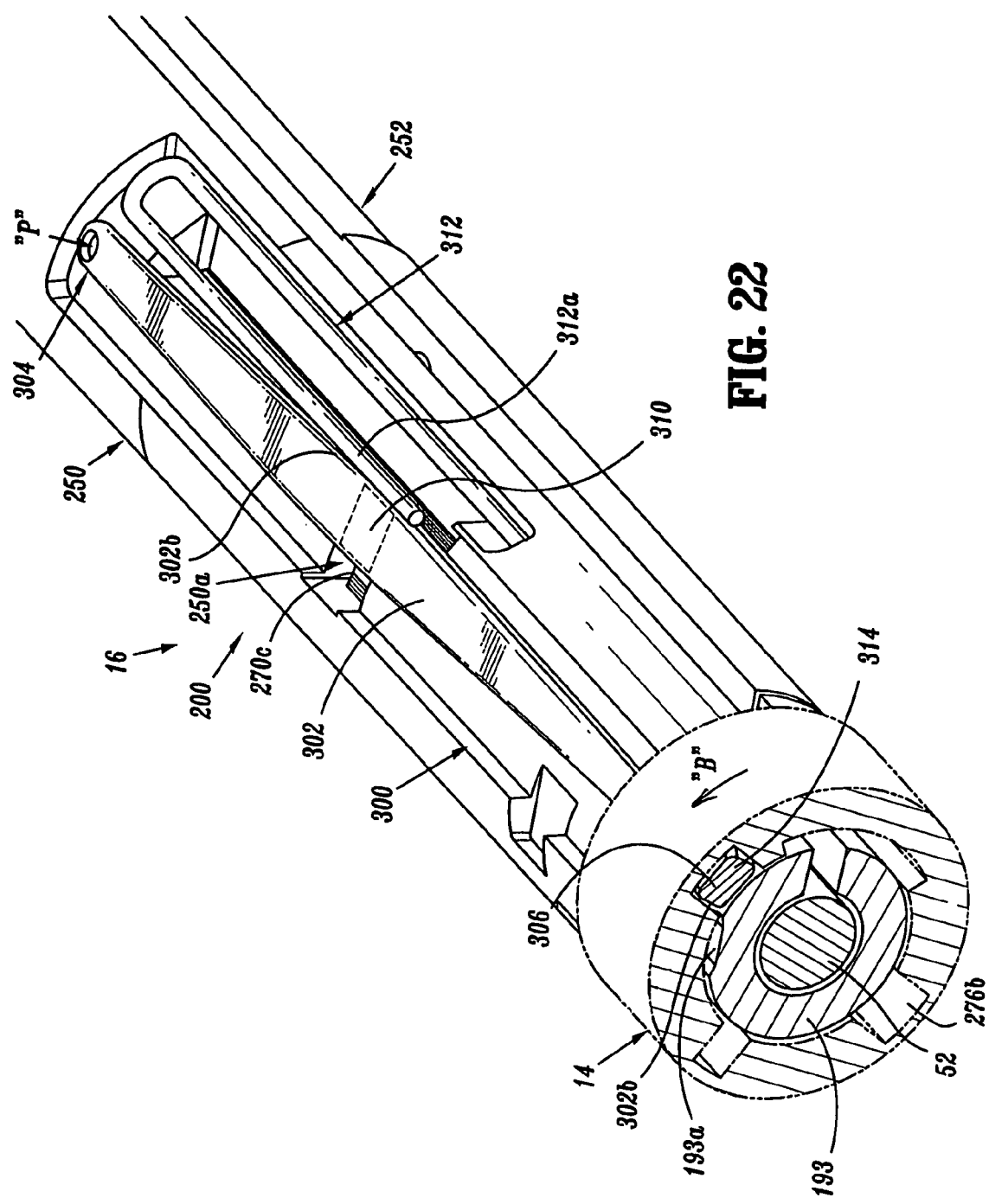
FIG. 22 is an enlarged transverse cross-sectional view of the proximal end of the DLU of FIGS. 6-9 with the distal end of the elongate body on the proximal end of the DLU as would be taken along 21-21 of FIG. 16, illustrating the locking mechanism in the second position.
Figure 23:
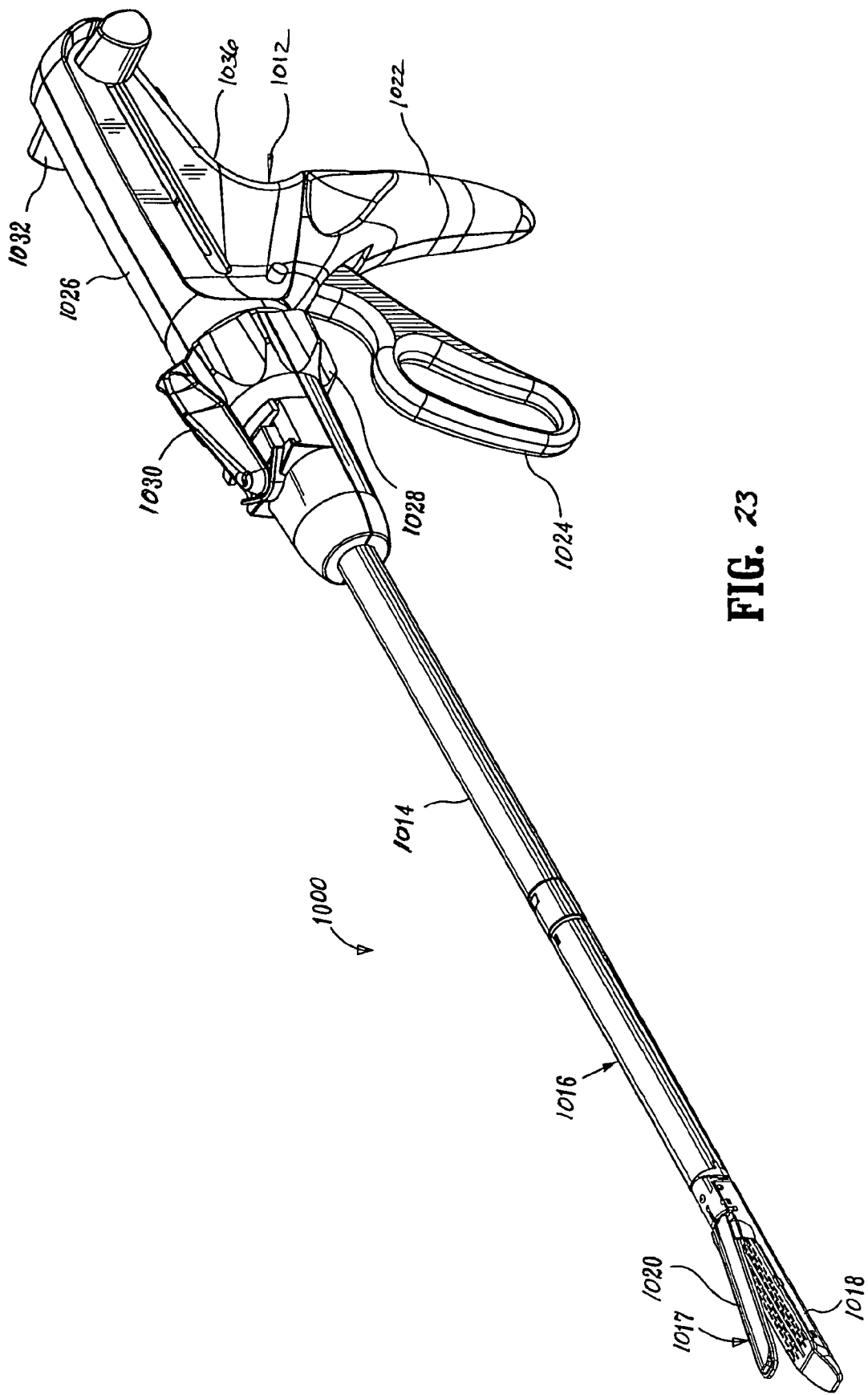
FIG. 23 is a top perspective view of a surgical stapling apparatus according to a further embodiment of the present disclosure.
Figure 24:
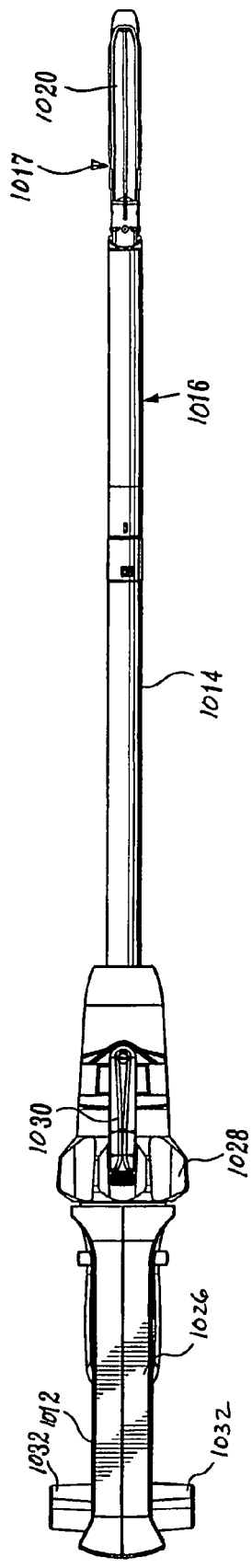
FIG. 24 is a top view of the surgical stapling apparatus shown in FIG. 23.
Figure 25:
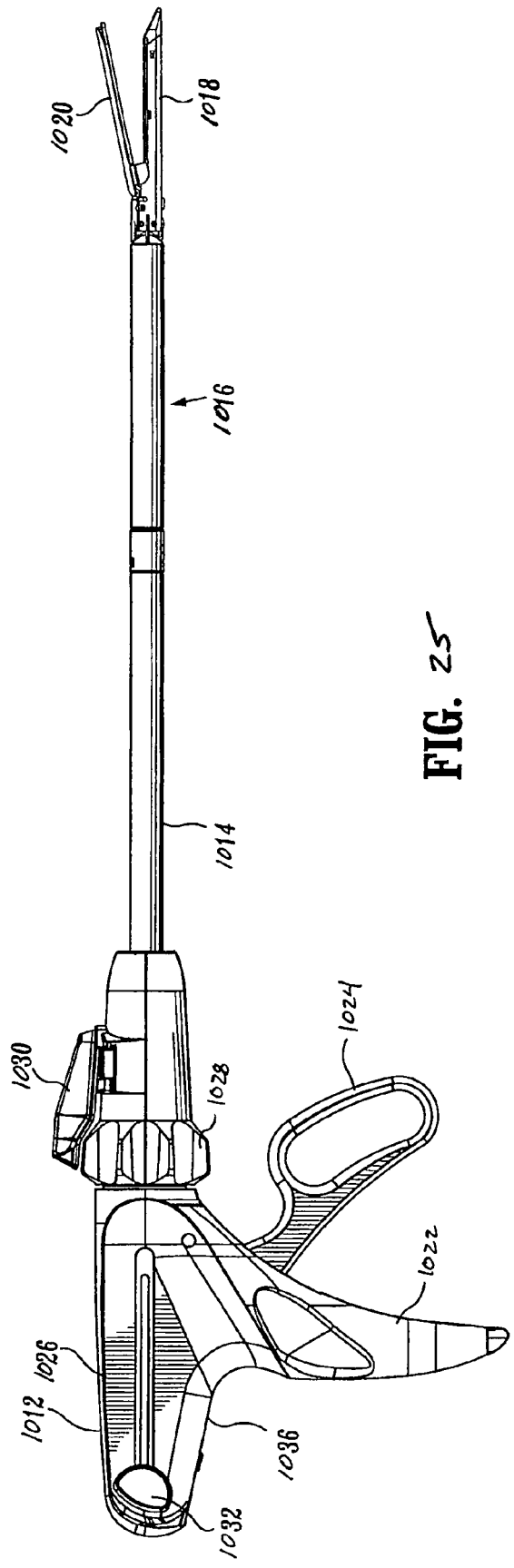
FIG. 25 is a side view of the surgical stapling apparatus shown in FIGS. 23 and 24.

When nubs 254 have reached slots 276e, and when insertion tip 193 has been fully inserted into the distal end of elongate body 14, DLU 16 is rotated, in the direction of arrow "B" (see FIG. 21). At this point in the coupling, rotation of DLU 16 results in three separate actions, namely, nubs 254 enter slots 276e, thus connecting DLU 16 to distal end 14 of stapling apparatus 10; projections 276b of firing rod 52 engage sections 270a and 270b of drive assembly 212, thus connecting firing rod 52 and drive assembly 212; and side wall of channel 276d urges lever 302 (such that side wall of channel 276d abuts against and engages proximal end of lever 306, preferably against a side surface 302b of lever 302) of locking mechanism 300 to pivot from the first position to the second position about pivot pin "P" to thereby disengage tooth 310 from shoulder 270c of engagement section 270 and thereby free drive assembly 212 to allow movement of drive assembly 212 and permit operation or continued operation of surgical stapling apparatus 10.

As can be appreciated, if lever 302 has been inadvertently moved to the second position, prior to coupling of DLU 16 to elongate body 14, and drive assembly 212 has prematurely moved from its proximal-most or ready-to-load position, lever 302 can not move to the first position since tooth 310 is not aligned with drive assembly 212 and can not pass in front of shoulder 270c. In such a situation, tooth 310 will abut against a portion of engagement section 270 to prevent lever 302 from returning to the first position. Thus, upon insertion of DLU 16 into elongate body 14, proximal end 306 of lever 302 will abut against and/or otherwise contact projection 276c of elongate body 14 and thus prevent loading of DLU 16 to elongate body 14.

Accordingly, the attachment of a DLU having a drive assembly which is not in its proximal-most or ready-to-load position is prevented.

Turning now to FIGS. 23-45, a surgical stapling apparatus, according to another embodiment of the present disclosure, is generally designated as 1000.

In the interest of brevity, only a discussion of the systems, methods and structures for loading, engaging, coupling or connecting a disposable loading unit ("DLU") 1016 to surgical stapling apparatus 1000 is provided. A detailed discussion of the remaining components and method of use of surgical stapling apparatus 1000, is disclosed in U.S. Pat. No. 6,241,139.

Surgical stapling apparatus 1000 is an endoscopic apparatus and includes a handle assembly 1012 and an elongated body 1014 extending from handle assembly 1012. A DLU 1016 is releasably secured to the distal end of elongated body 1014. While this disclosure relates to the use of a DLU with surgical stapling apparatus 1000, it is understood and within the scope of the present disclosure that a single use loading unit (SULU) or other end effector and/or tool assembly can equally be used in cooperation with surgical stapling apparatus 1000.

DLU 1016 includes a tool 1017 having a cartridge assembly 1018 housing a plurality of surgical staples (not shown) and an anvil assembly 1020 movably secured in relation to cartridge assembly 1018. As shown herein, DLU 1016 is configured to apply six (6) linear rows of staples, in DLU's measuring from about 30 mm to about 60 mm in length. DLUs for applying any number of rows of staples, having staple pockets arranged in various patterns and/or DLUs and end effectors having any other lengths, e.g., 45 mm, are also envisioned. Handle assembly 1012 includes a stationary handle member 1022, a movable handle member 1024, and a barrel portion 1026.

A rotatable member 1028 preferably is mounted on the forward end of barrel portion 1026 to facilitate rotation of elongated body 1014 and attached DLU 1016 with respect to handle assembly 1012. An articulation lever 1030 preferably is also mounted on the forward end of barrel portion 1026 adjacent rotatable member 1028 to facilitate articulation of tool assembly 1017. Preferably, a pair of knobs 1032 are movably positioned along barrel portion 1026. Knobs 1032 are advanced distally to approximate or close cartridge and/or anvil assembly 1018, 1020, and retracted proximally to unapproximate or open cartridge and/or anvil assembly 1018, 1020.

Figure 26:
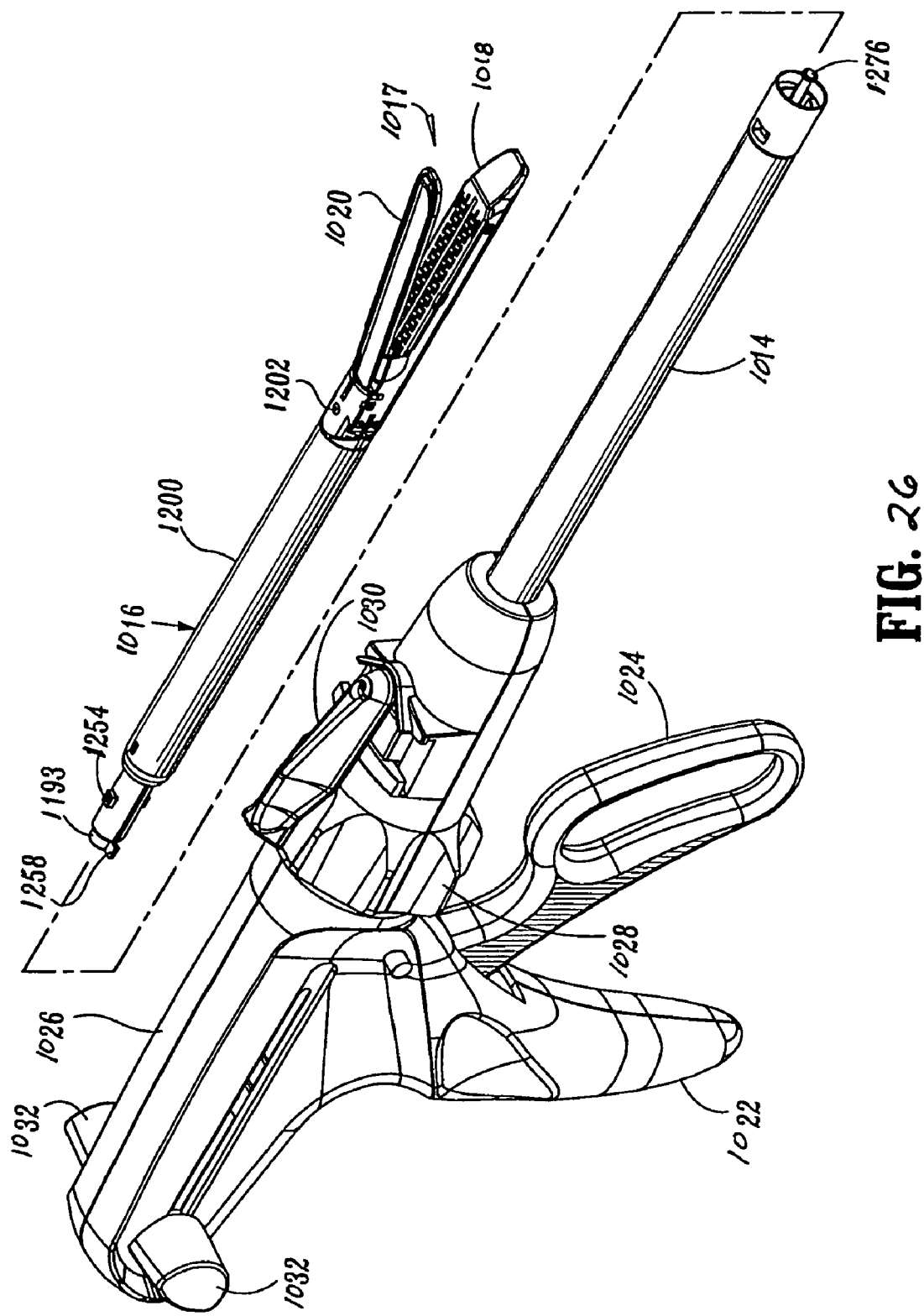
FIG. 26 is a top perspective view of the surgical stapling apparatus of FIGS. 23-25 with a DLU disengaged from the elongate body of the surgical stapling apparatus.

As seen in FIG. 26, DLU 1016 is desirably selectively removably couplable to elongated body 1014. DLU 1016 includes a housing portion 1200 having a proximal end adapted to releasably engage the distal end of elongated body 1014. A mounting assembly 1202 is pivotally secured at 1203 to the distal end of housing portion 1200, and is configured to receive the proximal end of tool assembly 1017 such that pivotal movement of mounting assembly 1202 about an axis at 1203 perpendicular to the longitudinal axis of housing portion 1200 effects articulation of tool assembly 1017.

Figure 27:
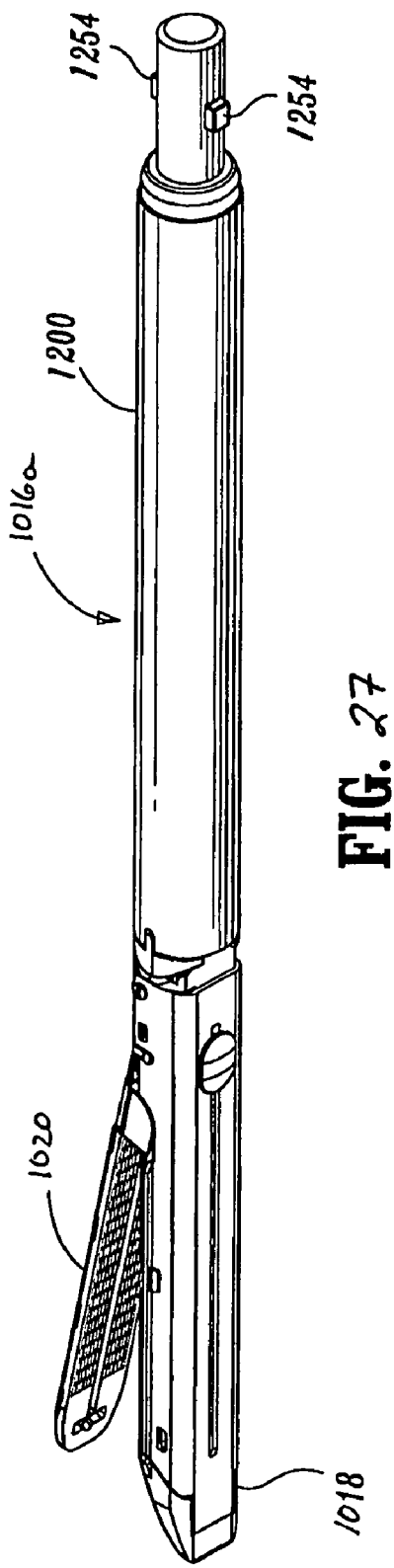
FIG. 27 is a bottom perspective view of a non-articulating DLU for use with the surgical stapling apparatus of FIGS. 23-26.
Figure 28:
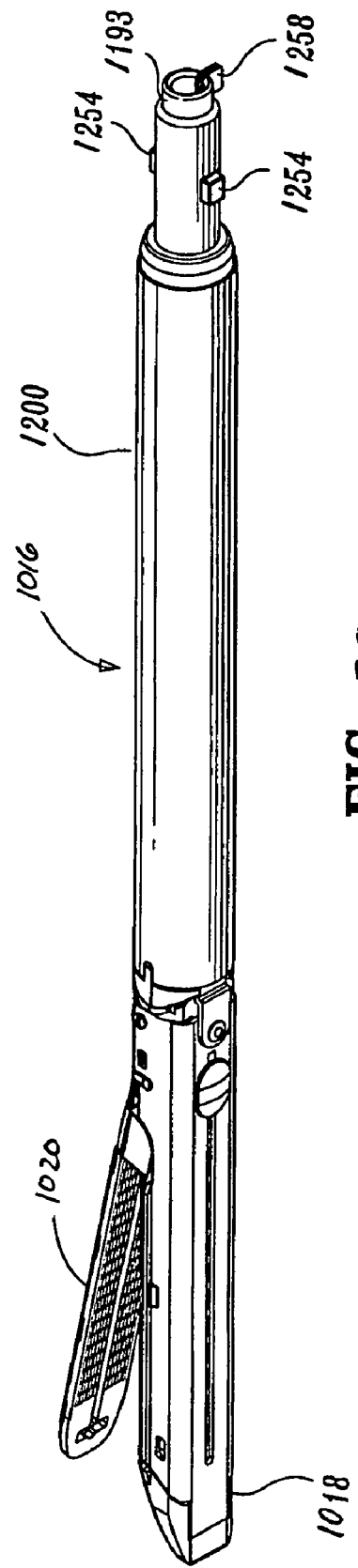
FIG. 28 is a bottom perspective view of the preferred articulating DLU of the surgical stapling apparatus of FIGS. 23-26.
Figure 29:
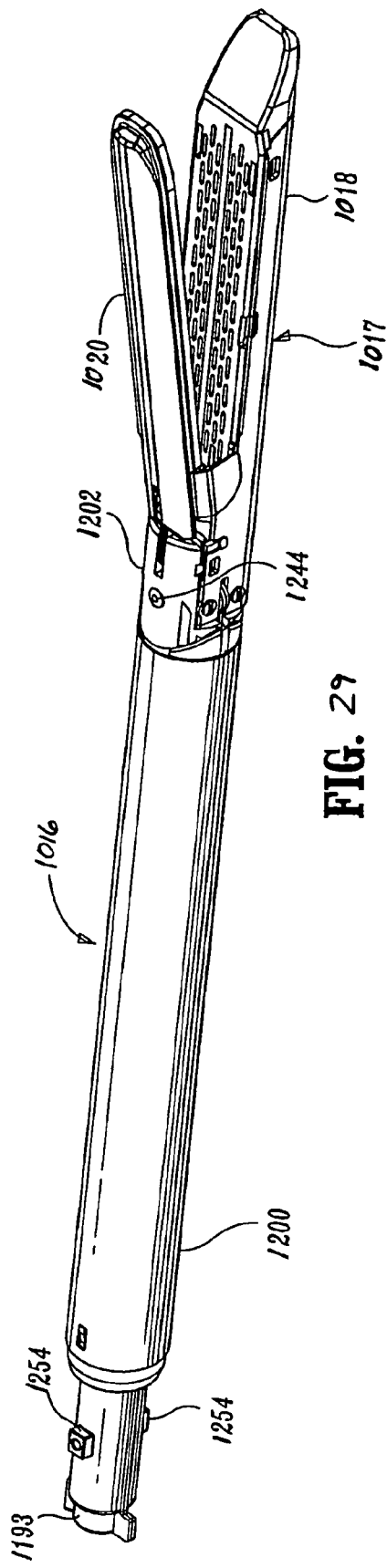
FIG. 29 is a top perspective view of the DLU of FIG. 28.
Figure 30:
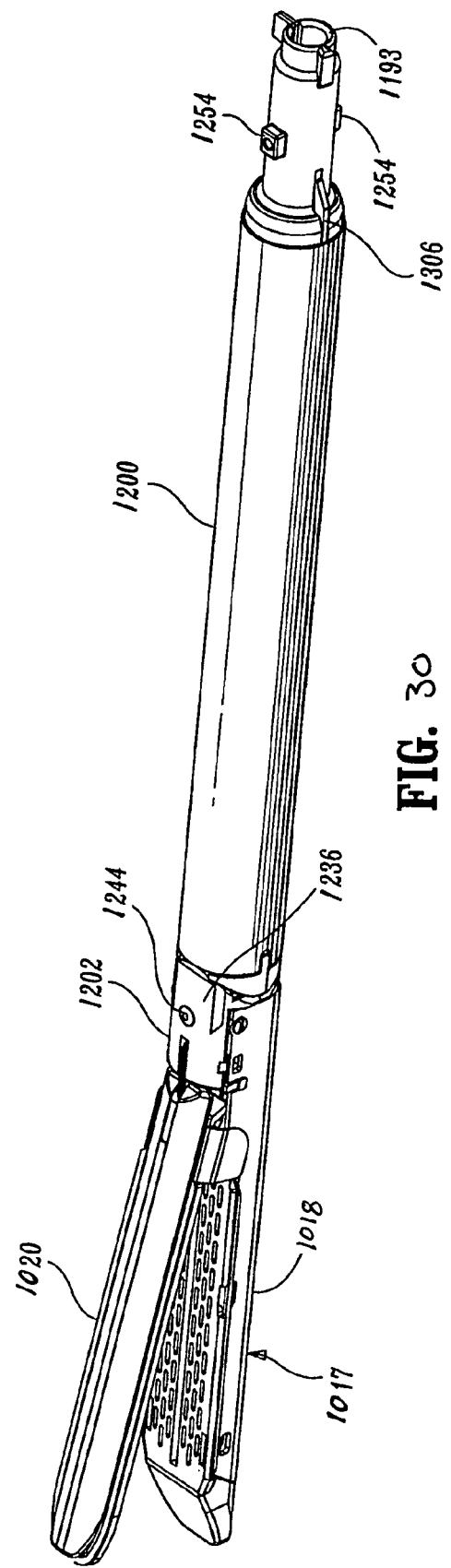
FIG. 30 is a top perspective view of the DLU of FIGS. 28 and 29.

Surgical stapling apparatus 1000 is capable of receiving a non-articulating DLU 1016a, as seen in FIG. 27, or an articulating DLU 1016, as seen in FIGS. 28-308. U.S. Pat. No. 6,241,139 includes a detailed discussion of articulating and non-articulating DLU.

With general reference to FIGS. 31, 31a, 32-35, 37 and 39-45 and particular reference to FIGS. 31, 31a, 37, 39 and 40, DLU 1016 includes a mounting assembly 1235. Mounting assembly 1235 includes an upper and a lower mounting portion 1236, 1238, respectively. A centrally located pivot member 1284 extends from each of upper and lower mounting portions 1236, 1238 through respective openings 1246a formed in coupling members 1246. Coupling members 1246 each include an interlocking proximal portion 1246b configured to be received in grooves 1290 formed in the proximal end of upper and lower housing halves 1250, 1252 to retain mounting assembly 1235 and upper and lower housing halves 1250, 1252 in a longitudinally fixed position in relation to each other.

Upper housing half 1250 and lower housing half 1252 are contained within an outer sleeve, shell or casing 1251. The proximal end of upper housing half 1250 includes radially outwardly extending engagement nubs 1254 for releasably engaging the distal end of body 1014. Nubs 1254 form a bayonet-type coupling with the distal end of body 1014. Housing halves 1250 and 1252 define a channel 1400 for slidably receiving axial drive assembly 1212 therein. An articulation link 1256 is dimensioned to be slidably positioned within a slot 1402 formed in upper and lower housing halves 1250, 1252. A pair of blow out plate assemblies 1255 are positioned adjacent the distal end of housing portion 1200 adjacent the distal end of axial drive assembly 1212 to prevent outward buckling and bulging of drive assembly 1212 during articulation and firing of surgical stapling apparatus 1000. For a detailed discussion of the structure and operation of blow out plate assemblies 1255, reference is made to International Application Serial No. PCT/US02/32031, filed on Oct. 4, 2002, entitled "Surgical Stapling Device", the entire content of which is herein incorporated by reference.

Figure 31:
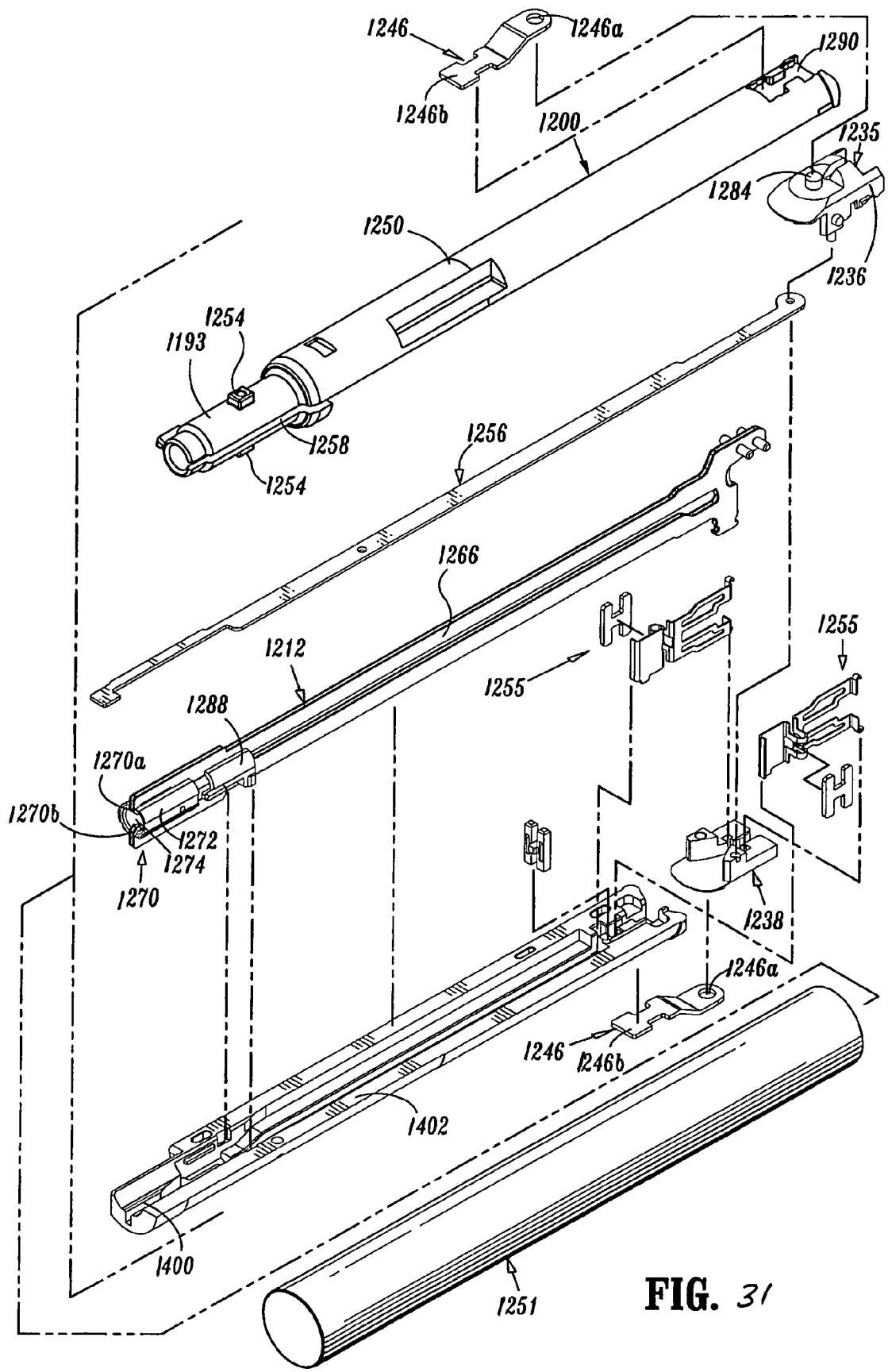
FIG. 31 is an enlarged top perspective view, with parts separated, of the proximal housing portion and mounting assembly of the DLU of FIGS. 28-30.
Figure 31A:
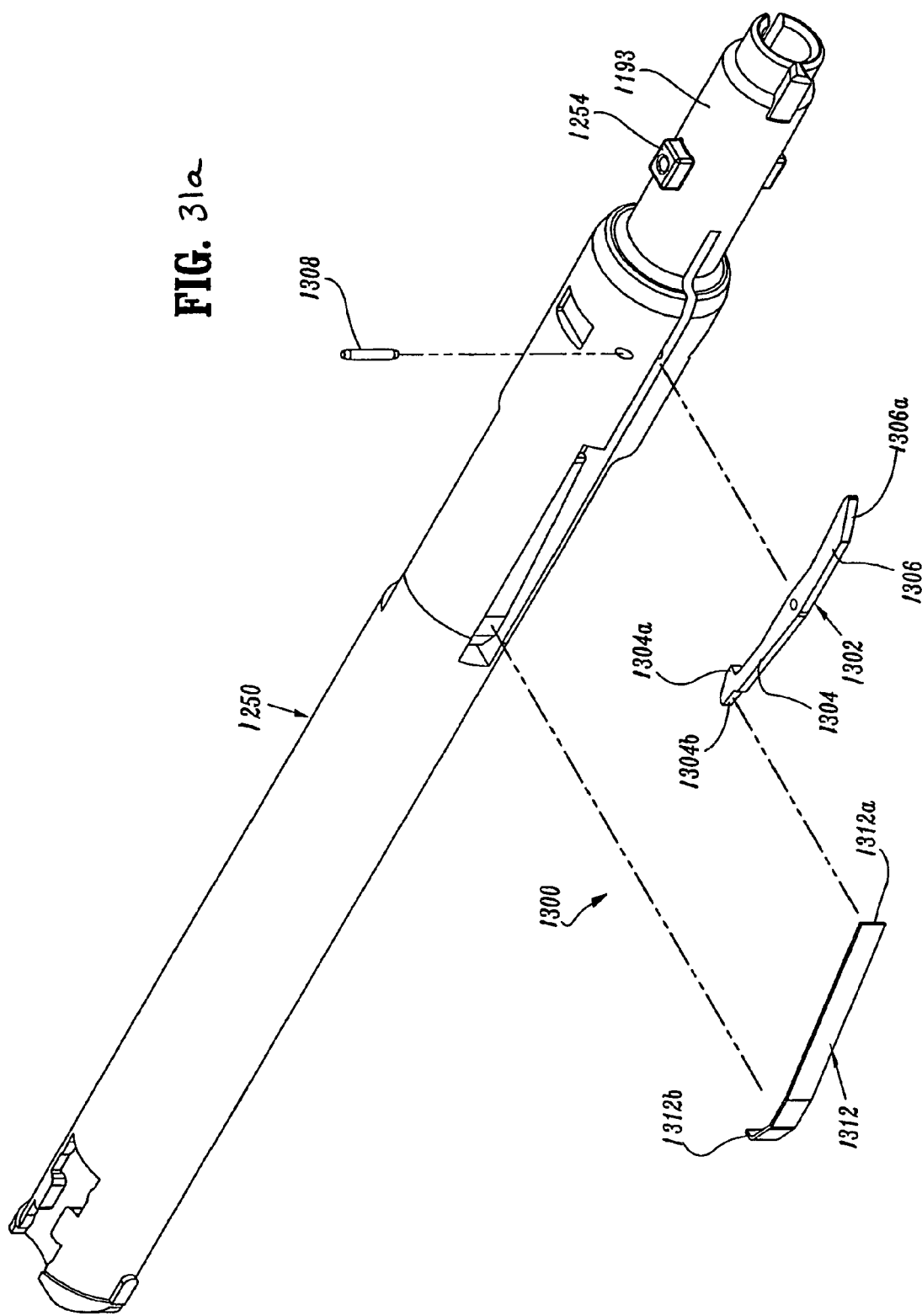
FIG. 31a is an enlarged top perspective view of the proximal portion of the upper housing half of the DLU of FIGS. 28-31.

Referring to FIG. 31, optionally, a locking member 1288 may be supported on engagement section 1270 of axial drive assembly 1212. In operation, when axial drive assembly 1212 is actuated, by applying a predetermined force to movable handle member 1024 to advance axial drive assembly 1212 distally, locking member 1288 provides an audible and tactile indication that surgical stapling apparatus 1000 has been actuated. For a detailed discussion of the structure and operation of locking member 1288, reference is made to the aforementioned International Application Serial No. PCT/US02/32031. Locking member 1288 may also prevent inadvertent partial actuation of DLU 1016, such as during shipping, by locking axial drive assembly 1212 at a fixed position within DLU 1016 until a predetermined axial force has been applied to axial drive assembly 1212.

Figure 33:
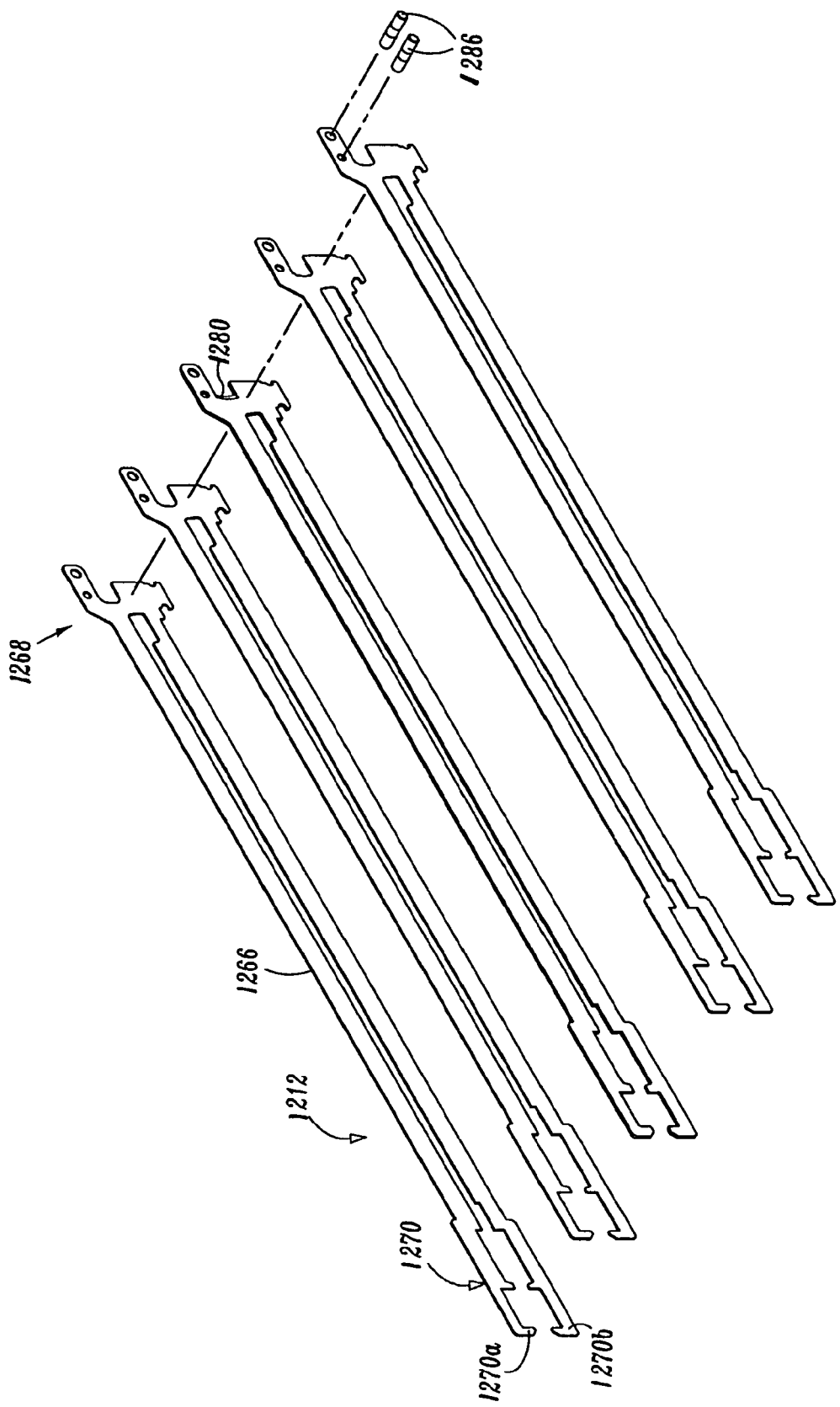
FIG. 33 is a top perspective view, with parts separated, of the axial drive assembly of the DLU of FIGS. 28-31.

With reference to FIGS. 31-34, axial drive assembly 1212 includes an elongated drive beam 1266 (FIG. 33) including a distal working head 1268 (FIG. 34) and a proximal engagement section 1270. Drive beam 1266 may be constructed from a single sheet of material or, preferably, multiple stacked sheets, as shown in FIG. 33. Engagement section 1270 includes a pair of resilient engagement fingers 1270a and 1270b which are dimensioned and configured to mountingly engage a pair of corresponding retention slots 1272a and 1272b formed in drive member 1272 (FIG. 34). Drive member 1272 includes a proximal porthole 1274 configured to receive distal end 1276 of a drive member, e.g., drive rod or control rod 1052 (FIGS. 36 and 38-40) when the proximal end of DLU 1016 is being engaged with elongated body 1014 of surgical stapling apparatus 1000. Control rod 1052 functions to impart axial movement of drive assembly 1212 from handle assembly 1012.

With reference to FIGS. 31, 31a and 37-45, DLU 1016 further includes a locking mechanism 1300, preferably pivotably supported on a housing, e.g., on upper housing half 1250. Locking mechanism 1300 is manipulatable from a first position, in which drive assembly 1212 is maintained in a ready-to-load position for proper loading, to a second position, in which drive assembly 1212 is free to move. DLU 1016 is considered to be loaded to elongate body 1014 when locking mechanism 1300 is in the second position, i.e., when drive assembly 1212 is connected to control rod 1052 of elongate body 1014. As seen in FIGS. 31, 31a and 37-45, locking mechanism 1300 includes a lever 1302 pivotally connected to upper housing half 1250 by a pivot pin 1308 extending therethrough, thereby defining a pivot point. Lever 1302 includes a free distal end 1304 extending distally of pivot pin 1308 and a free proximal end 1306 extending proximally of pivot pin 1308. Proximal end 1306 of lever 1302 terminates in an angled surface 1306a formed along an upper surface thereof for engaging a portion of elongate body 1014, as will be discussed in greater detail below. Distal end 1304 of lever 1302 terminates in a hook member 1304a formed along a lower surface thereof for engaging drive member 1272, as will be discussed in greater detail below.

Locking mechanism 1300 further includes a biasing member or spring 1312, preferably a leaf spring, operatively associated with upper housing half 1250 and distal end 1304 of lever 1302. Preferably, spring 1312 maintains lever 1302 in the first position such that hook member 1304a is engaged with drive member 1272. Spring 1312 includes a proximal end 1312a operatively associated with distal end 1304 of lever 1302, and a distal end 1312b secured to upper housing half 1250. Preferably, distal end 1312b is in the form of a hook or bent arm extending into a slot or groove 1250a (see FIGS. 39-42) in upper housing half 1250 in such a manner so as to create a force "F" acting radially inward at proximal end 1312a of spring 1312 (see FIG. 39). Proximal end 1312a is positioned in engagement with an outer surface 1304b of distal end 1304 of lever 1302. As such, force "F" in turn acts on distal end 1304 of lever 1302 to thereby urge distal end 1304 radially inward as well. In so doing, proximal end 1306 of lever 1302 is urged radially outward due to the pivoting action of lever 1302 about pivot pin 1308.

Figure 37:
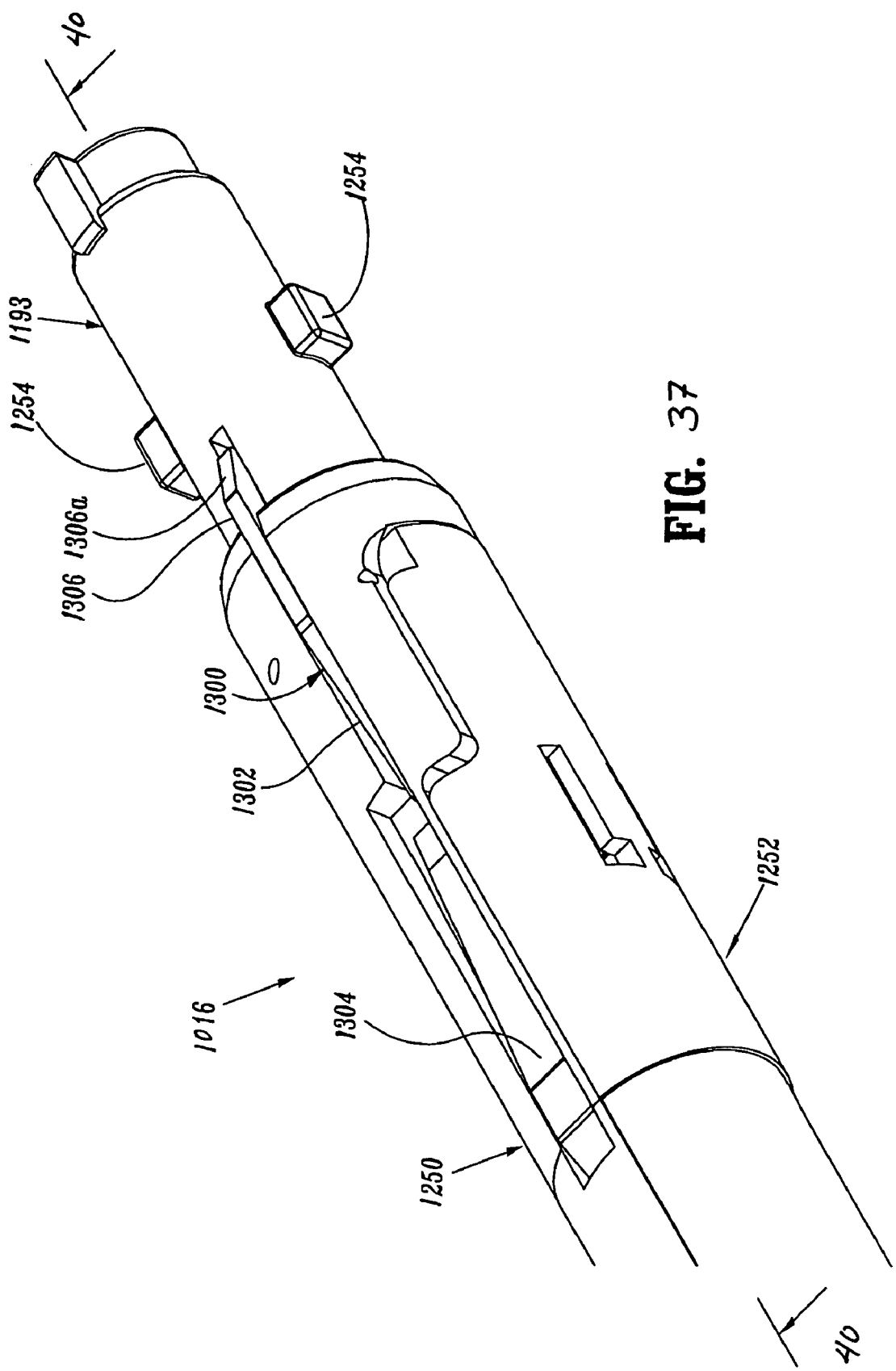
FIG. 37 is an enlarged perspective view of the proximal end of the DLU of FIGS. 28-31 illustrating a locking mechanism according to the present disclosure.
Figure 39:
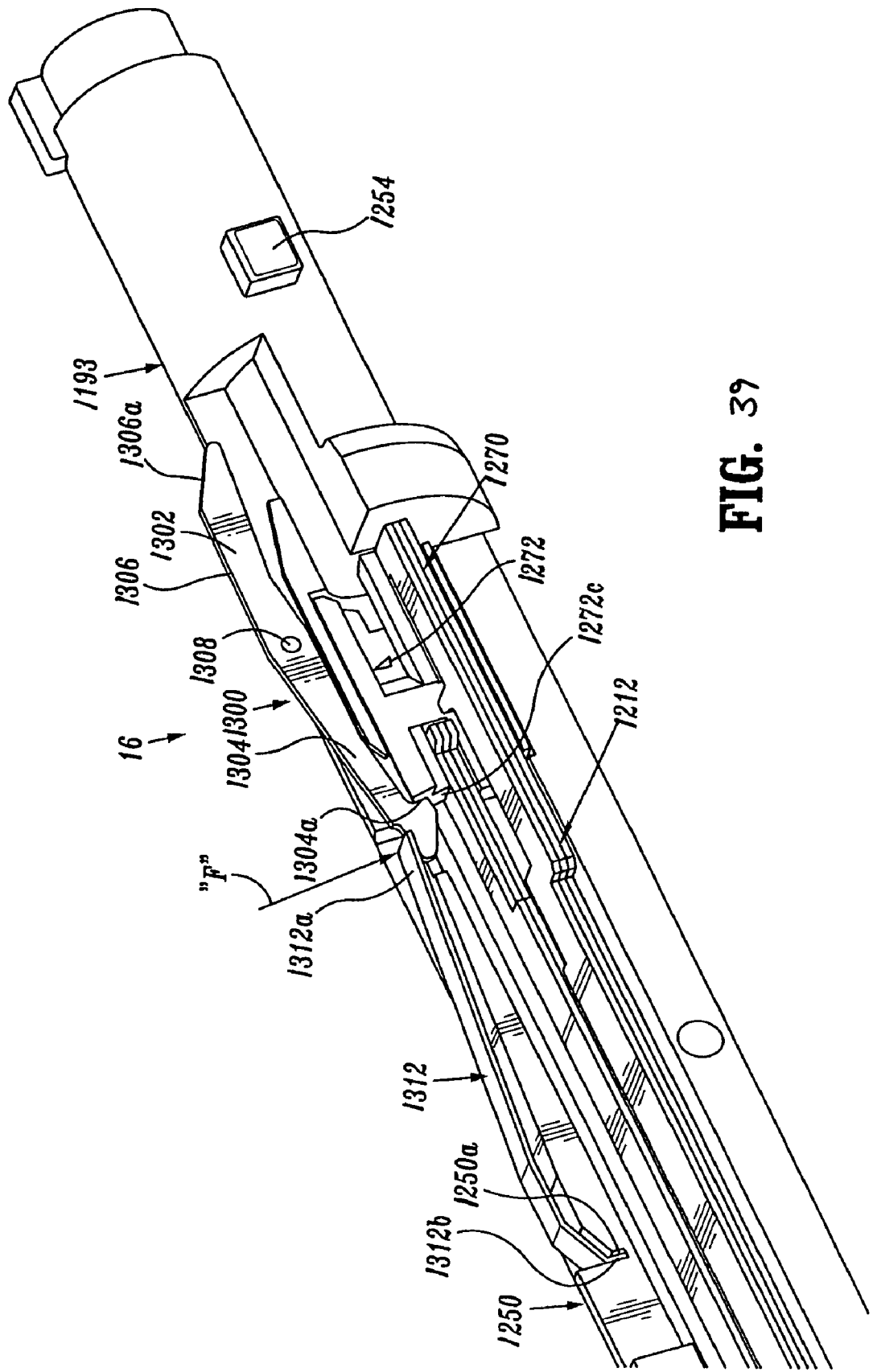
FIG. 39 is an enlarged perspective view, partially broken-away, of the proximal end of the DLU of FIG. 37 illustrating the locking mechanism in a first position.
Figure 40:
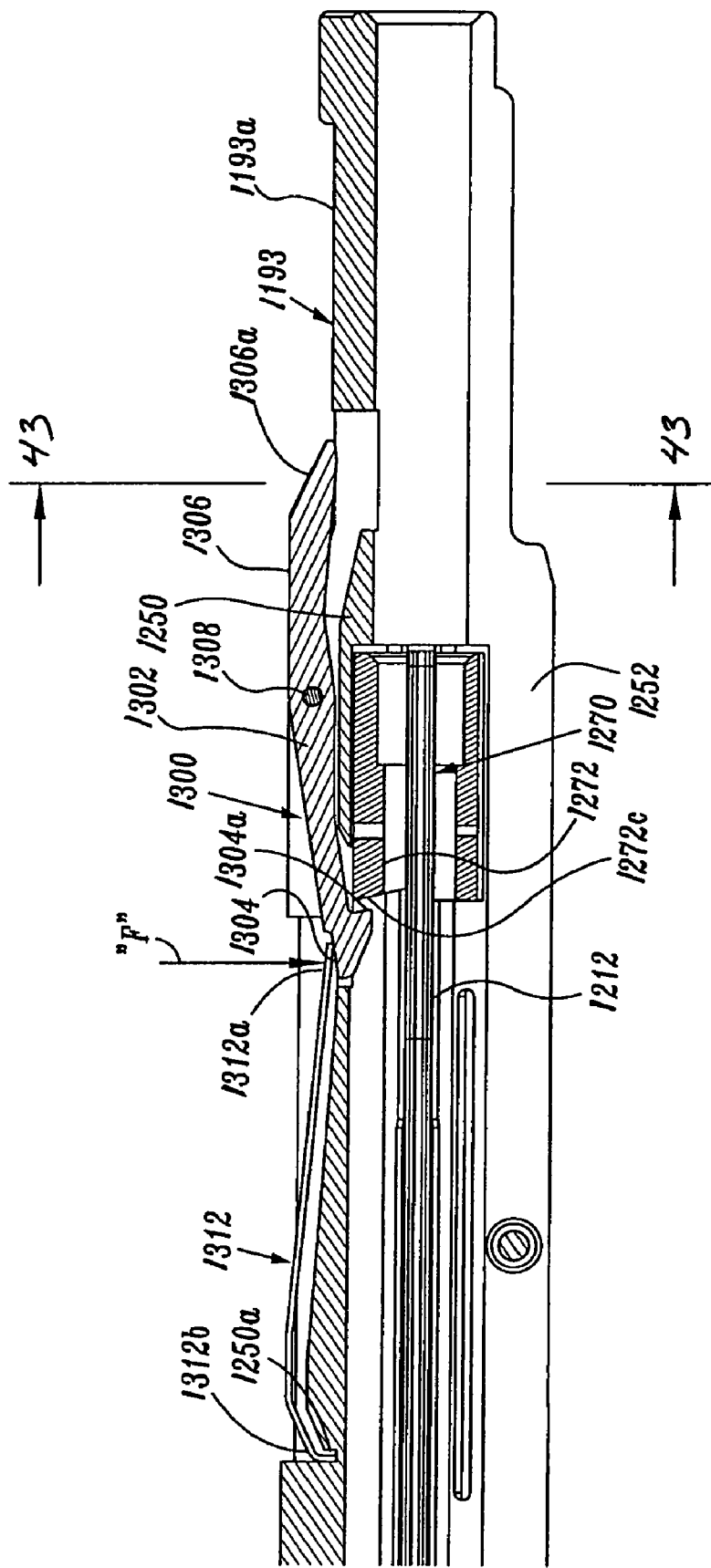
FIG. 40 is a longitudinal cross-sectional view of the proximal end of the DLU of FIGS. 28-31, as taken through 40-40 of FIG. 37, with the locking mechanism in a first position.

Prior to attachment of DLU 1016 to surgical stapling apparatus 1000, lever 1302 of locking mechanism 1300 is urged to the locked position by spring 1312 (FIGS. 37, 39 and 40). As discussed above, in the locked position, lever 1302 is pivoted about pivot pin 1308 such that hook member 1304a of lever 1302 is in engagement with a distal face 1272c of drive member 1272 and proximal end 1306 is positioned radially outward of an outer surface 1193a of insertion tip 1193 (see FIG. 40). In this locked position, hook member 1304a prevents inadvertent distal advancement of drive member 1272 to maintain drive member 1272 in its proximal-most ready-to-load position. This ensures that engagement section 1270 of drive assembly 1212 properly engages the distal end 1276 of control rod 1052 (see FIG. 36) of stapling apparatus 1000 when DLU 1016 is mounted to elongated body 1014 of stapling apparatus 1000. Distal end 1276 of control rod 1052 has one or more engagement surfaces, preferably, and here shown as, including a head 1276a and a smaller diameter annular recess 1276b just proximal of head 1276a and partially defined by head 1276a.

Figure 42:
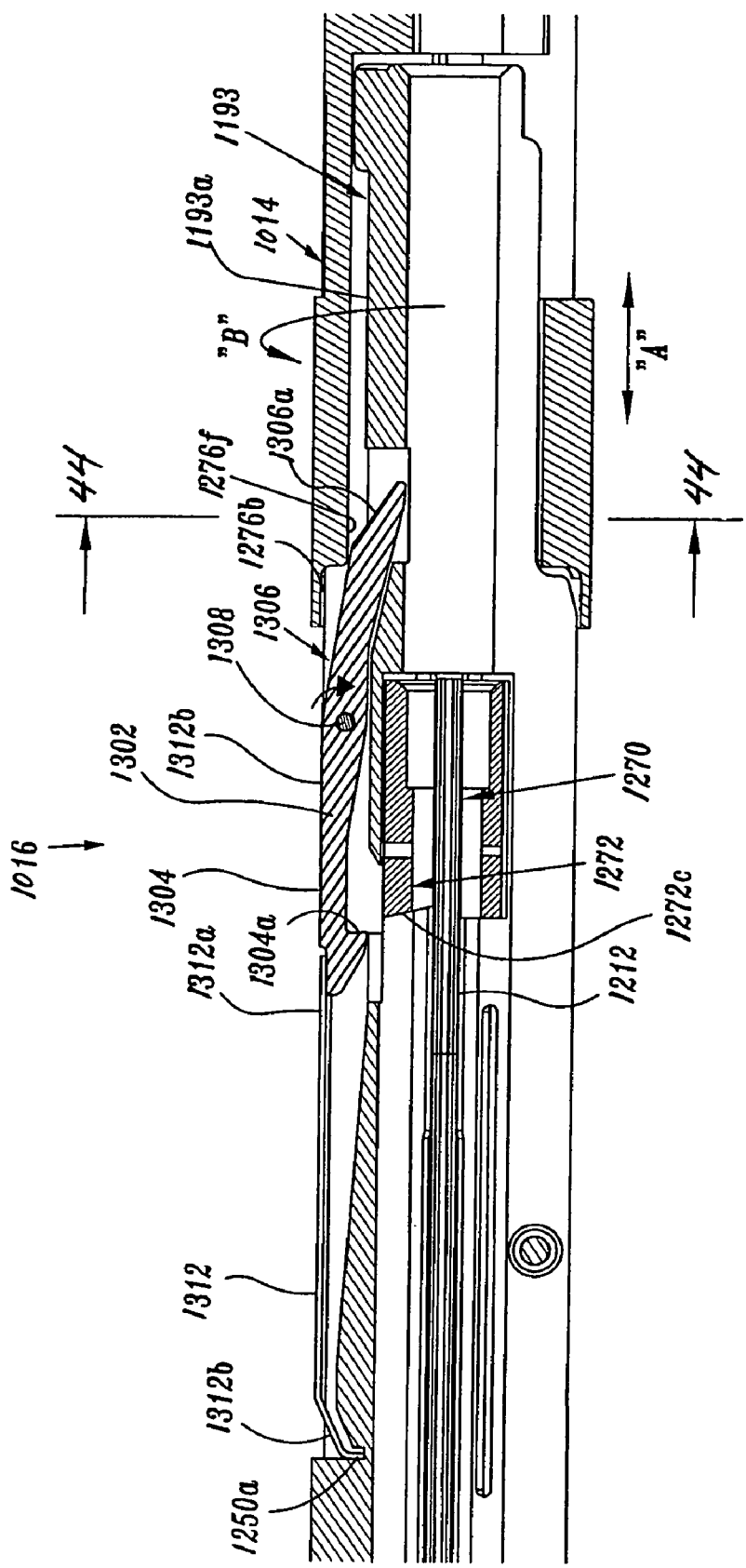
FIG. 42 is a longitudinal cross-sectional view of the proximal end of the DLU of FIGS. 28-31 as taken through 40-40 of FIG. 37, with the locking mechanism in a second position.

When DLU 1016 is mounted to elongated body 1014 of stapling apparatus 1000, in a manner to be discussed in further detail below, angled surface 1306a of proximal end 1306 of lever 1302 engages sloping surface 1276f of elongate body 1014 (see FIGS. 42, 44 and 45). Engagement between angled surface 1306a and sloping surface 1276f pivots or rotates lever 1302 about pivot pin 1308 to cam proximal end 1306 of lever 1302 radially inwardly. Movement of proximal end 1306 radially inwardly effects movement of hook 1304a radially outwardly against force "F" of spring 1312, such that hook 1304a is released from and/or otherwise disengaged from drive member 1272 to free drive assembly 1212 and enable the operation or continued operation of surgical stapling apparatus 1000.

Figure 38:
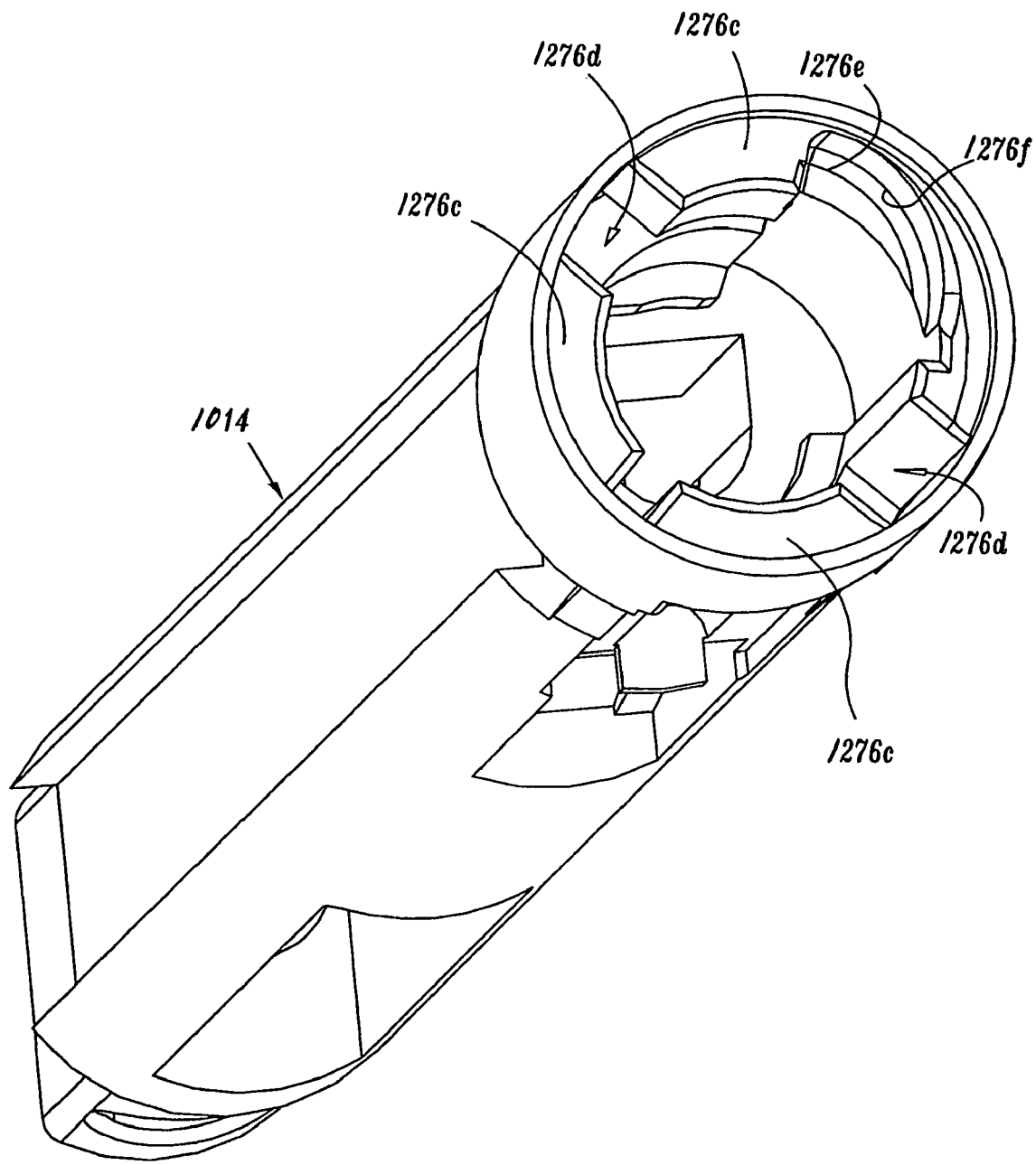
FIG. 38 is an enlarged perspective view of a distal end of the elongate body of the stapling apparatus in accordance with the present disclosure.

As best seen in FIG. 38, preferably the distal end of elongate body 1014 includes a recess 1276e formed therein having a shape to facilitate manipulation of locking mechanism 1300 from the first position to the second position. Preferably, recess 1276e includes a sloping surface 1276f against which angled surface 1306a of lever 1302 contacts. In particular, sloping surface 1276f is shaped such that twisting of DLU 1016 in relation to elongated body 1014 of stapling apparatus 1000, after insertion tip 1193 of DLU 1016 has been inserted into the distal end of elongate body 1014, results in proximal end 1306 of lever 1302 being progressively urged or cammed radially inward. Only after DLU 1016 has been rotated over a sufficient arc in relation to body 1014 will proximal end 1306 of lever 1302 be cammed radially inwardly a distance sufficient to release hook member 1304a from drive member 1272.

Figure 41:
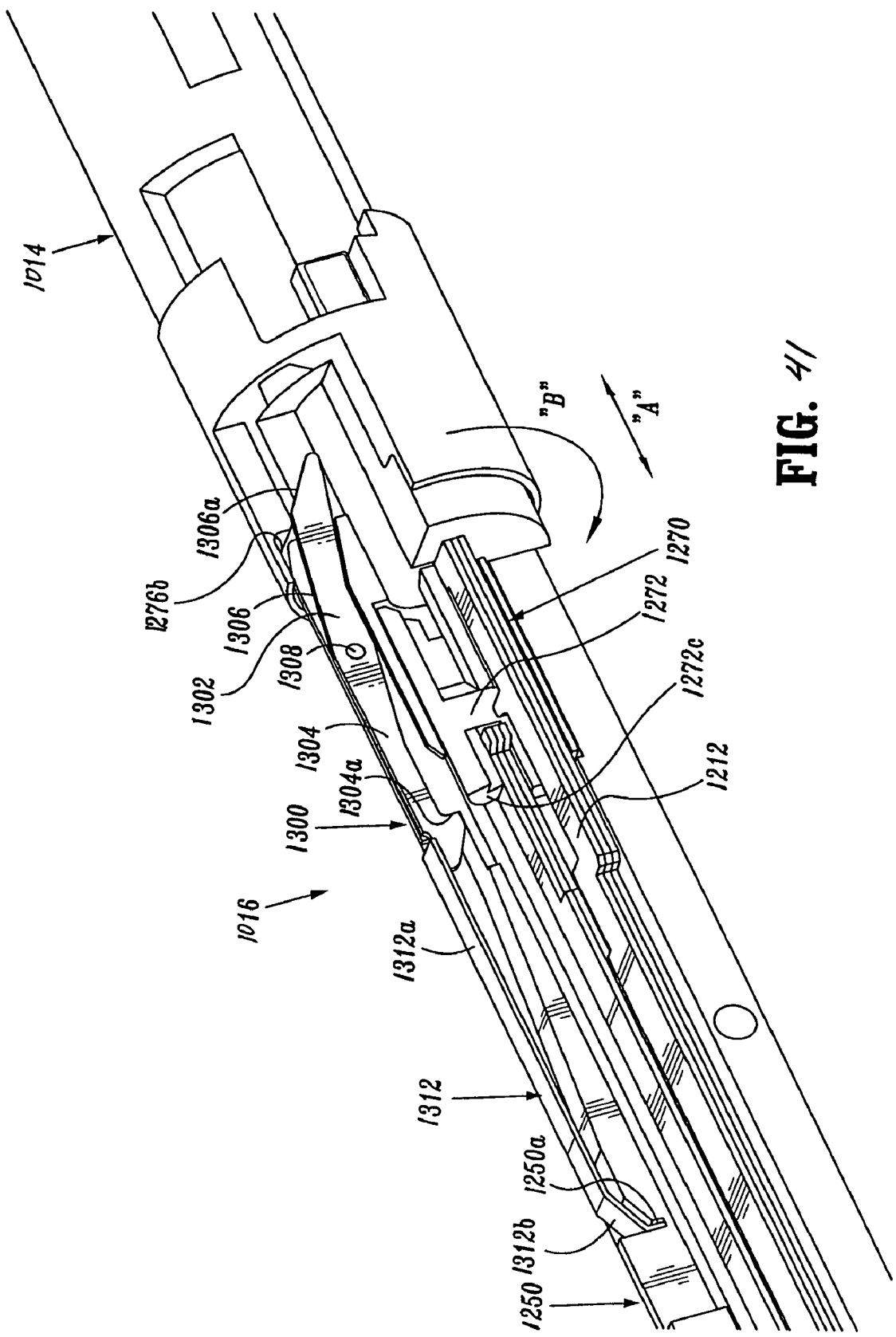
FIG. 41 is an enlarged perspective view, partially broken-away, of the proximal end of the DLU of FIG. 37 illustrating the locking mechanism in a second position.

With continued reference to FIGS. 37-45, a method of use and/or operation of locking mechanism 1300, when securing DLU 1016 to the distal end of elongate body 1014, will be discussed. Initially, with locking mechanism 1300 in the first position such that hook 1304a is in engagement with drive member 1272, insertion tip 1193 of DLU 1016 is introduced longitudinally into the distal end of elongate body 1014, in either direction of arrow "A" (FIG. 41). As seen in FIGS. 41, 42 and 44, during introduction of insertion tip 1193 into the distal end of elongate body 1014, proximal end 1306 of lever 1302 enters recess 1276b (FIG. 42) formed in the distal end of elongate body 1014.

When insertion tip 1193 has been fully inserted into the distal end of elongate body 1014, and more particularly, when nubs 1254 have completely entered channels 1276d (FIGS. 38, 44 and 45), DLU 1016 is rotated, in the direction of arrow "B" (FIGS. 41 and 45), such that sloping surface 1276f of recess 1276e acts against and engages angled surface 1306a of proximal end 1306 of lever 1302. As described above, the camming action between sloping surface 1276f of recess 1276e and angled surface 1306a of proximal end 1306 causes proximal end 1306 of lever 1302 to be urged radially inward, as indicated by arrow "C" of FIG. 45, and about pivot pin 1308, thereby overcoming force "F" of spring 1312, and urging distal end 1304 radially outward such that lever 1302 is urged from the first position to the second position. Displacement of distal end 1304 in a radially outward direction results in hook 1304a becoming disengaged from drive member 1272 thereby freeing drive assembly 1212 for the continued operation of surgical stapling apparatus 1000. DLU 1016 is considered to be loaded to elongate body 1014 when lever 1302 is in the second position, e.g., when drive assembly 1212 is connected to drive member or control rod 1052 of elongate body 1014.

Accordingly, the attachment of a DLU, having a drive assembly 1212, to the distal end of elongate body 1014 when drive assembly 1212 is not in its proximal-most or proper loading position is prevented.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto.

What is claimed is:

1. A surgical instrument, comprising:
   a handle assembly;
   a housing at least partially positioned distally of the handle assembly, the housing including an elongate body extending therefrom; and
   a loading unit removably supportable on a distal end of the housing, the loading unit including:
      a housing portion including a distal end and a proximal end;
      a drive assembly slidably supported within the housing portion of the loading unit; and
      a locking mechanism in the form of a lever having a distal end defining a hook for selectively engaging a portion of the drive assembly, the locking mechanism having a first position wherein the hook of the locking mechanism engages a portion of the drive assembly and maintains the position of the drive assembly relative to the housing portion of the loading unit, and the locking mechanism having a second position wherein the hook of the locking mechanism is disengaged from the drive assembly and enables the drive assembly to move relative to the housing portion,
   wherein the locking mechanism is configured for movement from the first position to the second position in response to a connection of the loading unit to the elongate body of the housing, whereupon during connection, the housing of the surgical instrument engages a proximal end of the lever to disengage to hook of the locking mechanism from the drive assembly.

2. The surgical apparatus of claim 1, wherein the lever is pivotably connected to the housing portion and defines a pivot point, the distal end of the lever extending distally of the pivot point and including the hook, and the proximal end of the lever extending proximally of the pivot point.

3. The surgical apparatus of claim 2, wherein when the locking mechanism is moved from the first position to the second position, the proximal end of the lever is moved radially inward relative to a central longitudinal axis of the loading unit and the distal end of the lever is moved radially outward relative to the central longitudinal axis of the loading unit.

4. The surgical apparatus of claim 3, wherein the locking mechanism is moved from the first position to the second position upon a coupling of the loading unit to a distal end of the elongate body.

5. The surgical apparatus of claim 4, wherein the loading unit and the elongate body are configured for twisting engagement with one another, and wherein the locking mechanism is moved from the first position to the second position by a twisting action of the loading unit relative to the elongate body when the proximal end of the housing portion of the loading unit is inserted in to the distal end of the elongate body.

6. The surgical apparatus of claim 5, wherein the locking mechanism further includes a biasing member operatively associated therewith, wherein the biasing member biases the lever to the first position.

7. The surgical apparatus of claim 6, wherein when the locking mechanism is in the first position, the proximal end of the lever extends radially beyond an outer surface of the housing portion.

8. The surgical apparatus of claim 7, wherein the proximal end of the lever of the locking mechanism defines an angled surface to facilitate connection with the elongate body.

9. The surgical apparatus of claim 8, further comprising an elongate body extending from the housing, the elongate body including a distal end configured and dimensioned to selectively receive the proximal end of the housing portion of the loading unit.

10. The surgical apparatus of claim 1, wherein the distal end of the lever is pivotably connected to the housing portion and the proximal end of the lever is free, the lever further including a tooth extending radially inward therefrom, wherein the tooth selectively engages an engagement surface formed on the drive assembly such that when the locking mechanism is in the first position the tooth engages the engagement surface of the drive assembly and when the locking mechanism is in the second position the tooth is disengaged from the engagement surface of the drive assembly.

11. The surgical apparatus of claim 10, wherein when the locking mechanism is moved from the first position to the second position, the lever is pivoted about the distal end thereof such that a longitudinal axis of the lever is angled with respect to a longitudinal axis of the housing portion.

12. The surgical apparatus of claim 11, wherein the locking mechanism is moved from the first position to the second position by a projection extending radially inward of the elongate body, the projection acting on a side surface of the lever as the loading unit is twisted into loaded engagement in the elongate body.

13. The surgical apparatus of claim 12, wherein when the locking mechanism is in the first position the lever is substantially axially aligned with a nub extending radially outward from the proximal end of the housing portion and when the locking mechanism is in the second position the lever is out of axial alignment with the nub of the insertion tip.

14. The surgical apparatus of claim 13, wherein the proximal end of the lever includes a nub extending toward the proximal end of the housing portion, and wherein the proximal end of the housing portion includes a recess formed in the surface thereof for receipt of the nub of the lever when the lever is in the first position.

15. The surgical apparatus of claim 10, wherein the locking mechanism further includes a biasing member operatively associated therewith, wherein the biasing member tends to maintain the lever in the first position.

16. The surgical apparatus of claim 1, wherein the surgical apparatus is a stapler.

17. The surgical apparatus of claim 1, further comprising an elongate body extending from the housing.

18. The surgical apparatus of claim 1, wherein the proximal end of the housing portion of the loading unit defines an insertion tip.

19. The surgical instrument of claim 1, wherein the loading unit extends along a longitudinal axis and further includes an end effector with an anvil and a cartridge connected such that at least one of the anvil and the cartridge is movable relative to the longitudinal axis of the end effector for repositioning the end effector between open and closed positions.

20. The surgical instrument of claim 19, wherein the cartridge includes a plurality of surgical fasteners arranged into at least two rows extending along the longitudinal axis of the loading unit.

21. A loading unit for use with a surgical stapling apparatus including a handle assembly and a housing including an elongate body at least partially positioned distally of the handle assembly, the loading unit being configured and dimensioned to be removably supportable on a distal end of the elongate body of the housing and comprising:
a housing portion including a distal end and an elongate body extending from the distal end thereof;
a drive assembly slidably supported within the housing portion of the loading unit; and
a locking mechanism in the form of a lever having a distal end defining a hook for selectively engaging a portion of the drive assembly, the locking mechanism having a first position wherein the hook engages a portion of the drive assembly and maintains the position of the drive assembly relative to the housing portion of the loading unit, and the locking mechanism having a second position wherein the hook is disengaged from the drive assembly and enables the drive assembly to move relative to the housing portion,
wherein the locking mechanism is configured for movement from the first position to the second position in response to a connection of the loading unit to the elongate body of the housing, whereupon during connection, the housing of the surgical instrument engages a proximal end of the lever to disengage to hook from the drive assembly.

22. The loading unit of claim 21, wherein the lever is pivotably connected to the housing portion and defines a pivot point, the distal end of the lever extending distally of the pivot point and including the hook, and the proximal end of the lever extending proximally of the pivot point.

23. The loading unit of claim 21, wherein when the locking mechanism is moved from the first position to the second position, the proximal end of the lever is moved radially inward relative to a central longitudinal axis of the loading unit and the distal end of the lever is moved radially outward relative to the central longitudinal axis of the loading unit.

24. The loading unit of claim 23, wherein the locking mechanism is moved from the first position to the second position upon a coupling of the elongate body of the loading unit to a free end of the elongate body of the surgical stapling apparatus.

25. The loading unit of claim 24, wherein the elongate body of the loading unit and the elongate body of the surgical stapling apparatus are configured for twisting engagement with one another, and wherein the locking mechanism is moved from the first position to the second position by a twisting action of the loading unit relative to the elongate body of the surgical stapling apparatus when the elongate body of the loading unit is inserted in to the free end of the elongate body of the surgical stapling apparatus.

26. The loading unit of claim 25, wherein the locking mechanism further includes a biasing member operatively associated therewith, wherein the biasing member biases the lever to the first position.

27. The loading unit of claim 26, wherein when the locking mechanism is in the first position, the proximal end of the lever extends radially beyond an outer surface of the housing portion.

28. The loading unit of claim 27, wherein the proximal end of the lever of the locking mechanism defines an angled surface to facilitate connection with the elongate body of the loading unit.

29. The loading unit of claim 21, wherein the locking mechanism includes:
a lever having a distal end pivotably connected to the housing portion and a free proximal end; and
a tooth extending radially inward from the lever, wherein the tooth selectively engages an engagement surface formed on the drive assembly such that when the locking mechanism is in the first position the tooth engages the engagement surface of the drive assembly and when the locking mechanism is in the second position the tooth is disengaged from the engagement surface of the drive assembly.

30. The loading unit of claim 29, wherein when the locking mechanism is moved from the first position to the second position, the lever is pivoted about the distal end thereof such that a longitudinal axis of the lever is angled with respect to a longitudinal axis of the housing portion.

31. The loading unit of claim 30, wherein the locking mechanism is moved from the first position to the second position by a projection extending radially inward of the elongate body, the projection acting on a side surface of the lever as the loading unit is twisted into loaded engagement in the elongate body.

32. The loading unit of claim 31, wherein when the locking mechanism is in the first position the lever is substantially axially aligned with a nub extending radially outward from the proximal end of the housing portion and when the locking mechanism is in the second position the lever is out of axial alignment with the nub of the proximal end of the housing portion.

33. The loading unit of claim 32, wherein the proximal end of the lever includes a nub extending toward the proximal end of the housing portion, and wherein the insertion tip includes a recess formed in the surface thereof for receipt of the nub of the lever when the lever is in the first position.

34. The loading unit of claim 33, wherein the locking mechanism further includes a biasing member operatively associated therewith, wherein the biasing member tends to maintain the lever in the first position.

35. The loading unit of claim 21, wherein the proximal end of the housing portion of the loading unit defines an insertion tip.

36. The loading unit of claim 21, wherein the loading unit functions as a stapler.

37. The loading unit of claim 21, wherein the housing portion of the loading unit includes a proximal end configured for releasable support on the distal end of the elongate body of the surgical stapling apparatus.

38. The loading unit of claim 21, wherein the loading unit extends along a longitudinal axis and further includes an end effector with an anvil and a cartridge connected such that at least one of the anvil and the cartridge is movable relative to the longitudinal axis of the end effector for repositioning the end effector between open and closed positions.

39. The loading unit of claim 38, wherein the cartridge includes a plurality of surgical fasteners arranged into at least two rows extending along the longitudinal axis of the loading unit.

40. A surgical instrument comprising:
a housing including an elongate body extending therefrom;
a drive member at least partially positioned within the housing; and a loading unit supportable on a distal end of the housing, the loading unit including:

a housing portion including a distal end and a proximal end;

a drive assembly slidably supported within the housing portion of the loading unit and connectable to the drive member of the surgical instrument; and a locking mechanism in the form of a lever having a first end defining a hook for selectively engaging a portion of the drive assembly, the locking mechanism having a first position wherein the hook of the locking mechanism engages a portion of the drive assembly and maintains the position of the drive assembly relative to the housing portion of the loading unit, and the locking mechanism having a second position wherein the hook of the locking mechanism is disengaged from the drive assembly and enables the drive assembly to move relative to the housing portion, wherein the locking mechanism is configured for movement from the first position to the second position in response to a connection of the loading unit to the elongate body of the housing, whereupon during connection, the housing of the surgical instrument engages a second end of the lever to disengage to hook of the locking mechanism from the drive assembly.

41. The surgical instrument of claim 40, wherein the loading unit extends along a longitudinal axis and further includes an end effector with an anvil and a cartridge connected such that at least one of the anvil and the cartridge is movable relative to the longitudinal axis of the end effector for repositioning the end effector between open and closed positions.

42. The loading unit of claim 41, wherein the cartridge includes a plurality of surgical fasteners arranged into at least two rows extending along the longitudinal axis of the loading unit.

* * * * *